(12) United States Patent
Spann

(10) Patent No.: US 9,451,940 B2
(45) Date of Patent: Sep. 27, 2016

(54) METHOD OF RETROPERITONEAL LATERAL INSERTION OF SPINAL IMPLANTS

(75) Inventor: Scott Spann, Austin, TX (US)

(73) Assignee: Pantheon Spinal, LLC, Austin, TX (US)

(*) Notice: Subject to any disclaimer, the term of this patent is extended or adjusted under 35 U.S.C. 154(b) by 0 days.

(21) Appl. No.: 13/239,014

(22) Filed: Sep. 21, 2011

(65) Prior Publication Data

US 2012/0010715 A1 Jan. 12, 2012

Related U.S. Application Data

(63) Continuation of application No. 13/133,909, filed as application No. PCT/US2009/069476 on Dec. 23, 2009.

(60) Provisional application No. 61/140,926, filed on Dec. 26, 2008, provisional application No. 61/178,315, filed on May 14, 2009.

(51) Int. Cl.
*A61F 2/44* (2006.01)
*A61B 17/02* (2006.01)
(Continued)

(52) U.S. Cl.
CPC .................. *A61B 17/02* (2013.01); *A61F 2/44* (2013.01); *A61F 2/4455* (2013.01);
(Continued)

(58) Field of Classification Search
CPC ............ A61F 2002/30538; A61F 2250/0006; A61F 2/4455
USPC ........... 623/17.11, 17.16; 600/210, 213–217, 600/219, 222
See application file for complete search history.

(56) References Cited

U.S. PATENT DOCUMENTS 1,706,500 A 3/1929 Smith
4,934,352 A 6/1990 Sullivan
(Continued)

FOREIGN PATENT DOCUMENTS

WO 2005030318 4/2005
WO 2006042241 4/2006
(Continued)

OTHER PUBLICATIONS

Watkins, Robert, "Surgical Approaches to the Spine". May 20, 1983, Springer-Verlag (pp. 112-116).*
(Continued)

*Primary Examiner* — Jan Christopher Merene
*Assistant Examiner* — Atiya Mahmud
(74) *Attorney, Agent, or Firm* — Meyertons, Hood, Kivlin, Kowert & Goetzel, P.C.; Eric B. Meyertons

(57) ABSTRACT

A method is disclosed for introducing a spinal disc implant into an intervertebral space of a subject. The subject is placed in a lateral position, and the anterior face of the spinal disc intervertebral space is accessed, between the L5 and S1 vertebrae, from an anterior and lateral retroperitoneal approach. An operative corridor to the anterior face of the spinal disc space is established by introducing a retractor instrument anterolaterally to the spinal disc space between the anterior superior iliac spine and the anterior inferior iliac spine. The damaged spinal disc contents are removed from the intervertebral space through the operative corridor, and the implant is advanced into the intervertebral space at an oblique angle and pivoted to position the implant substantially laterally within the intervertebral space. Elongated retractor and insertion instruments, as well as a modified disc implant, are also disclosed for carrying out the method.

40 Claims, 22 Drawing Sheets

(51) Int. Cl.
*A61F 2/46* (2006.01)
*A61F 2/30* (2006.01)

(52) U.S. Cl.
CPC ............ *A61F 2/4611* (2013.01); *A61F 2/4465* (2013.01); *A61F 2/4684* (2013.01); *A61F 2002/30538* (2013.01); *A61F 2002/30772* (2013.01); *A61F 2002/30777* (2013.01); *A61F 2002/30784* (2013.01); *A61F 2002/30843* (2013.01); *A61F 2002/4475* (2013.01); *A61F 2002/4627* (2013.01); *A61F 2002/4629* (2013.01); *A61F 2250/0006* (2013.01)

(56) References Cited

U.S. PATENT DOCUMENTS

| | | | |
|---|---|---|---|
| 5,297,538 A | 3/1994 | Daniel | |
| 5,514,180 A | 5/1996 | Heggeness et al. | |
| 5,599,279 A | 2/1997 | Slotman et al. | |
| 5,609,635 A | 3/1997 | Michelson | |
| 5,772,661 A | 6/1998 | Michelson | |
| 5,776,199 A | 7/1998 | Michelson | |
| 5,860,973 A | 1/1999 | Michelson | |
| 5,895,352 A | 4/1999 | Kleiner | |
| 5,931,777 A | 8/1999 | Sava | |
| 5,944,658 A | 8/1999 | Koros et al. | |
| 5,984,922 A | 11/1999 | McKay | |
| 6,030,401 A | 2/2000 | Marino | |
| 6,042,540 A | 3/2000 | Johnston et al. | |
| 6,080,155 A | 6/2000 | Michelson | |
| 6,139,493 A | 10/2000 | Koros et al. | |
| 6,143,032 A | 11/2000 | Schafer et al. | |
| 6,159,215 A | 12/2000 | Urbahns et al. | |
| 6,183,517 B1 * | 2/2001 | Suddaby | A61F 2/4455 623/17.16 |
| 6,221,082 B1 | 4/2001 | Marino et al. | |
| 6,224,603 B1 | 5/2001 | Marino | |
| 6,245,108 B1 | 6/2001 | Biscup | |
| 6,251,140 B1 | 6/2001 | Marino et al. | |
| 6,266,394 B1 | 7/2001 | Marino | |
| 6,280,447 B1 | 8/2001 | Marino et al. | |
| 6,290,724 B1 | 9/2001 | Marino | |
| 6,312,443 B1 | 11/2001 | Stone | |
| 6,368,325 B1 | 4/2002 | McKinley et al. | |
| 6,387,070 B1 | 5/2002 | Marino et al. | |
| 6,387,130 B1 | 5/2002 | Stone et al. | |
| 6,416,465 B2 | 7/2002 | Brau | |
| 6,466,817 B1 | 10/2002 | Kaula et al. | |
| 6,478,805 B1 | 11/2002 | Marino et al. | |
| 6,485,518 B1 | 11/2002 | Cornwall et al. | |
| 6,491,626 B1 | 12/2002 | Stone et al. | |
| 6,500,128 B2 | 12/2002 | Marino | |
| 6,519,319 B1 | 2/2003 | Marino et al. | |
| 6,533,797 B1 | 3/2003 | Stone et al. | |
| 6,540,747 B1 | 4/2003 | Marino | |
| 6,564,078 B1 | 5/2003 | Marino et al. | |
| 6,764,452 B1 | 7/2004 | Gillespie et al. | |
| 6,802,844 B2 | 10/2004 | Ferree | |
| 6,852,126 B2 | 2/2005 | Ahlgren | |
| 6,887,248 B2 | 5/2005 | McKinley et al. | |
| 6,923,814 B1 | 8/2005 | Hildebrand et al. | |
| 6,945,973 B2 | 9/2005 | Bray | |
| 6,964,674 B1 | 11/2005 | Matsuura et al. | |
| 7,025,769 B1 | 4/2006 | Ferree | |
| 7,050,848 B2 | 5/2006 | Hoey et al. | |
| 7,115,132 B2 | 10/2006 | Errico et al. | |
| 7,125,380 B2 | 10/2006 | Yager | |
| 7,156,875 B2 | 1/2007 | Michelson | |
| 7,162,850 B2 | 1/2007 | Marino et al. | |
| 7,166,113 B2 | 1/2007 | Arambula et al. | |
| 7,169,182 B2 | 1/2007 | Errico et al. | |
| 7,177,677 B2 | 2/2007 | Kaula et al. | |
| 7,207,949 B2 | 4/2007 | Miles et al. | |
| 7,207,991 B2 | 4/2007 | Michelson | |
| 7,235,081 B2 | 6/2007 | Errico et al. | |
| 7,235,082 B2 | 6/2007 | Bartish et al. | |
| 7,261,688 B2 | 8/2007 | Smith et al. | |
| 7,288,093 B2 | 10/2007 | Michelson | |
| 7,320,688 B2 | 1/2008 | Foley et al. | |
| 7,326,216 B2 | 2/2008 | Bertagnoli et al. | |
| 7,341,587 B2 | 3/2008 | Molz et al. | |
| 7,341,590 B2 | 3/2008 | Ferree | |
| 7,361,193 B2 | 4/2008 | Frey et al. | |
| 7,452,359 B1 | 11/2008 | Michelson | |
| 7,455,692 B2 | 11/2008 | Michelson | |
| 7,462,195 B1 | 12/2008 | Michelson | |
| 7,470,236 B1 | 12/2008 | Kelleher et al. | |
| 7,473,222 B2 | 1/2009 | Dewey et al. | |
| 7,476,252 B2 | 1/2009 | Foley | |
| 7,481,812 B2 | 1/2009 | Frey et al. | |
| 7,485,146 B1 | 2/2009 | Crook et al. | |
| 7,491,205 B1 | 2/2009 | Michelson | |
| 7,503,933 B2 | 3/2009 | Michelson | |
| 7,513,869 B2 | 4/2009 | Branch et al. | |
| 7,522,953 B2 | 4/2009 | Kaula et al. | |
| 7,524,285 B2 | 4/2009 | Branch et al. | |
| 7,527,649 B1 | 5/2009 | Blain | |
| 7,819,801 B2 | 10/2010 | Miles et al. | |
| 8,394,144 B2 * | 3/2013 | Zehavi et al. | 623/17.11 |
| 8,506,629 B2 | 8/2013 | Weiland | |
| 2002/0120336 A1 * | 8/2002 | Santilli | 623/17.16 |
| 2002/0165612 A1 | 11/2002 | Gerber et al. | |
| 2003/0233147 A1 | 12/2003 | Nicholson et al. | |
| 2004/0024291 A1 * | 2/2004 | Zinkel | 600/218 |
| 2004/0106927 A1 * | 6/2004 | Ruffner et al. | 606/90 |
| 2004/0117020 A1 | 6/2004 | Frey et al. | |
| 2004/0176665 A1 | 9/2004 | Branch et al. | |
| 2005/0043796 A1 | 2/2005 | Grant et al. | |
| 2005/0071009 A1 | 3/2005 | Muhanna et al. | |
| 2005/0149035 A1 | 7/2005 | Pimenta et al. | |
| 2006/0069315 A1 | 3/2006 | Miles et al. | |
| 2006/0195017 A1 | 8/2006 | Shluzas et al. | |
| 2006/0224044 A1 | 10/2006 | Marchek et al. | |
| 2006/0229627 A1 | 10/2006 | Hunt et al. | |
| 2007/0055109 A1 | 3/2007 | Bass et al. | |
| 2007/0093850 A1 | 4/2007 | Harris et al. | |
| 2007/0156026 A1 | 7/2007 | Frasier et al. | |
| 2007/0173941 A1 | 7/2007 | Allard | |
| 2007/0179611 A1 | 8/2007 | DiPoto et al. | |
| 2007/0203580 A1 | 8/2007 | Yeh | |
| 2007/0208227 A1 | 9/2007 | Smith et al. | |
| 2007/0213826 A1 | 9/2007 | Smith et al. | |
| 2007/0225726 A1 | 9/2007 | Dye et al. | |
| 2007/0225808 A1 | 9/2007 | Warnick | |
| 2007/0255415 A1 * | 11/2007 | Edie et al. | 623/17.16 |
| 2007/0282449 A1 * | 12/2007 | de Villiers | A61F 2/4425 623/17.15 |
| 2008/0021285 A1 | 1/2008 | Drzyzga et al. | |
| 2008/0058606 A1 | 3/2008 | Miles et al. | |
| 2008/0091211 A1 | 4/2008 | Gately | |
| 2008/0097164 A1 | 4/2008 | Miles et al. | |
| 2008/0119851 A1 * | 5/2008 | Shelokov | 606/61 |
| 2008/0140085 A1 | 6/2008 | Gately et al. | |
| 2008/0183046 A1 | 7/2008 | Boucher et al. | |
| 2008/0215153 A1 * | 9/2008 | Butterman et al. | 623/17.16 |
| 2008/0221694 A1 | 9/2008 | Warnick et al. | |
| 2008/0300688 A1 * | 12/2008 | Cannon et al. | 623/17.16 |
| 2009/0030423 A1 | 1/2009 | Puno | |
| 2009/0043345 A1 | 2/2009 | Mathews | |
| 2009/0099660 A1 * | 4/2009 | Scifert et al. | 623/17.16 |
| 2009/0259108 A1 * | 10/2009 | Miles et al. | 600/202 |
| 2010/0094422 A1 | 4/2010 | Hansell et al. | |
| 2012/0010472 A1 | 1/2012 | Spann | |
| 2012/0010715 A1 | 1/2012 | Spann | |
| 2012/0010716 A1 | 1/2012 | Spann | |

(56) References Cited

U.S. PATENT DOCUMENTS

2012/0010717 A1     1/2012   Spann
2012/0035730 A1     2/2012   Spann

FOREIGN PATENT DOCUMENTS

WO        2007016247     2/2007
WO        2010075555     1/2010

OTHER PUBLICATIONS

USPTO Non-Final Office Action for U.S. Appl. No. 13/133,909, mailed Jul. 13, 2012.
USPTO Final Office Action for U.S. Appl. No. 13/133,909, mailed Mar. 20, 2013.
USPTO Advisory Action for U.S. Appl. No. 13/133,909, mailed Jul. 2, 2013.
Extended European Search Report for European Patent Application No. EP09835860, date of completion: Feb. 7, 2013. (6 pages).
USPTO Non-Final Office Action for U.S. Appl. No. 13/239,014, mailed Feb. 21, 2013.
USPTO Non-Final Office Action for U.S. Appl. No. 13/239,024, mailed Dec. 20, 2012.
USPTO Non-Final Office Action for U.S. Appl. No. 13/239,042, mailed Mar. 6, 2013.
USPTO Requirement for Restriction/Election for U.S. Appl. No. 13/239,053, mailed Nov. 2, 2012.
USPTO Non-Final Office Action for U.S. Appl. No. 13/239,053, mailed Jan. 29, 2013.
Co-Pending U.S. Appl. No. 13/169,919 by Spann entitled "Minimally-Invasive Retroperitoneal Lateral Approach for Spinal Surgery" filed Jun. 27, 2011.
International Search Report and Written Opinion for PCT/US2009/069476, mailed Aug. 17, 2010. (5 pages).
USPTO Final Office Action for U.S. Appl. No. 13/239,024, mailed Jul. 19, 2013.
USPTO Final Office Action for U.S. Appl. No. 13/239,053, mailed Oct. 18, 2013.
USPTO Non-Final Office Action for U.S. Appl. No. 13/239,024, mailed Jan. 28, 2014.
USPTO Advisory Action for U.S. Appl. No. 13/239,042, mailed Feb. 6, 2014.
USPTO Advisory Action for U.S. Appl. No. 13/239,053, mailed Feb. 13, 2014.
Gumbs et al., "The Open Anterior Paramedian Retroperitoneal Approach for Spine Procedures," Arch Surg. 140:339-343, Apr. 2005.
Gumbs et al., "Open Anterior Approaches for Lumbar Spine Procedures," The American Journal of Surgery 194:98-102, 2007.
USPTO Final Office Action for U.S. Appl. No. 13/239,014, mailed Oct. 30, 2013.
USPTO Final Office Action for U.S. Appl. No. 13/239,042, mailed Oct. 30, 2013.

\* cited by examiner

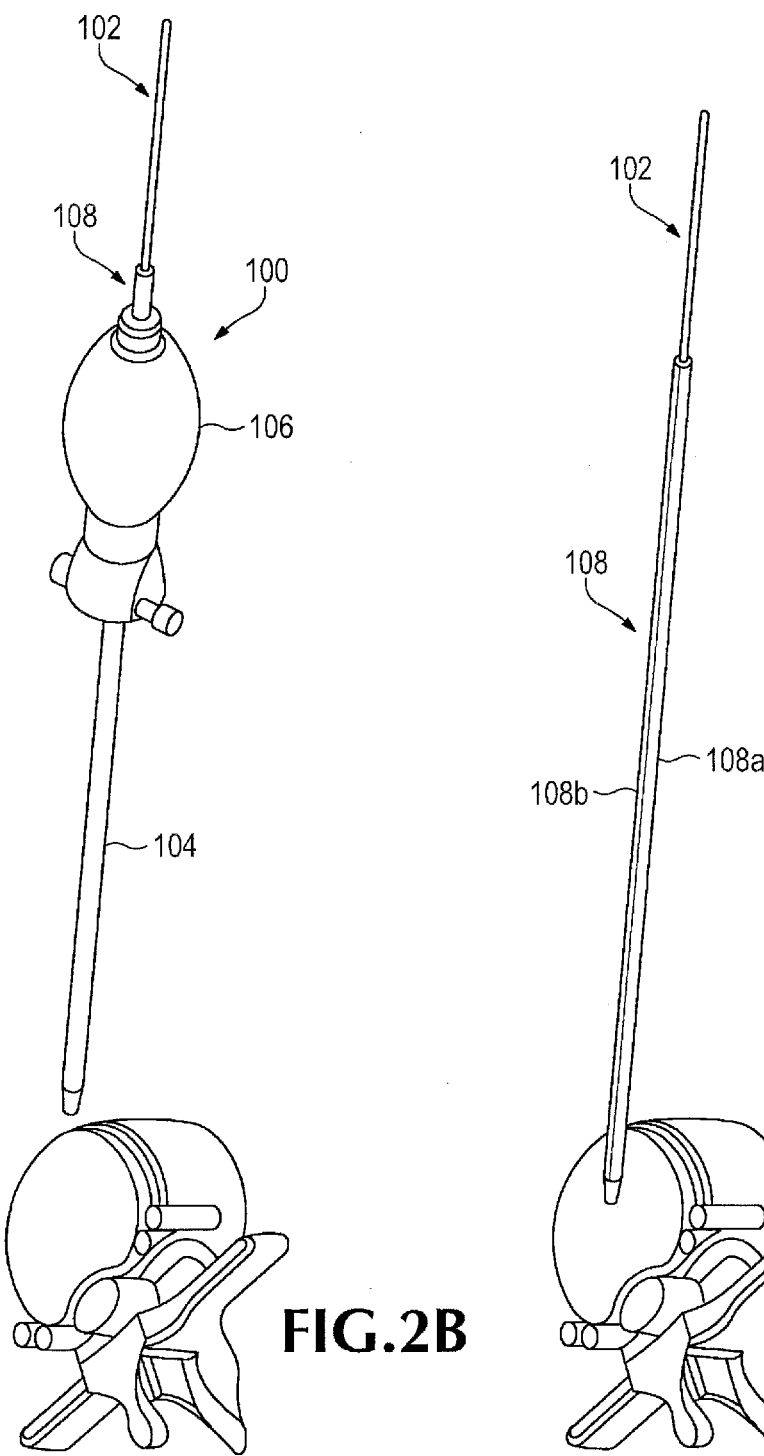

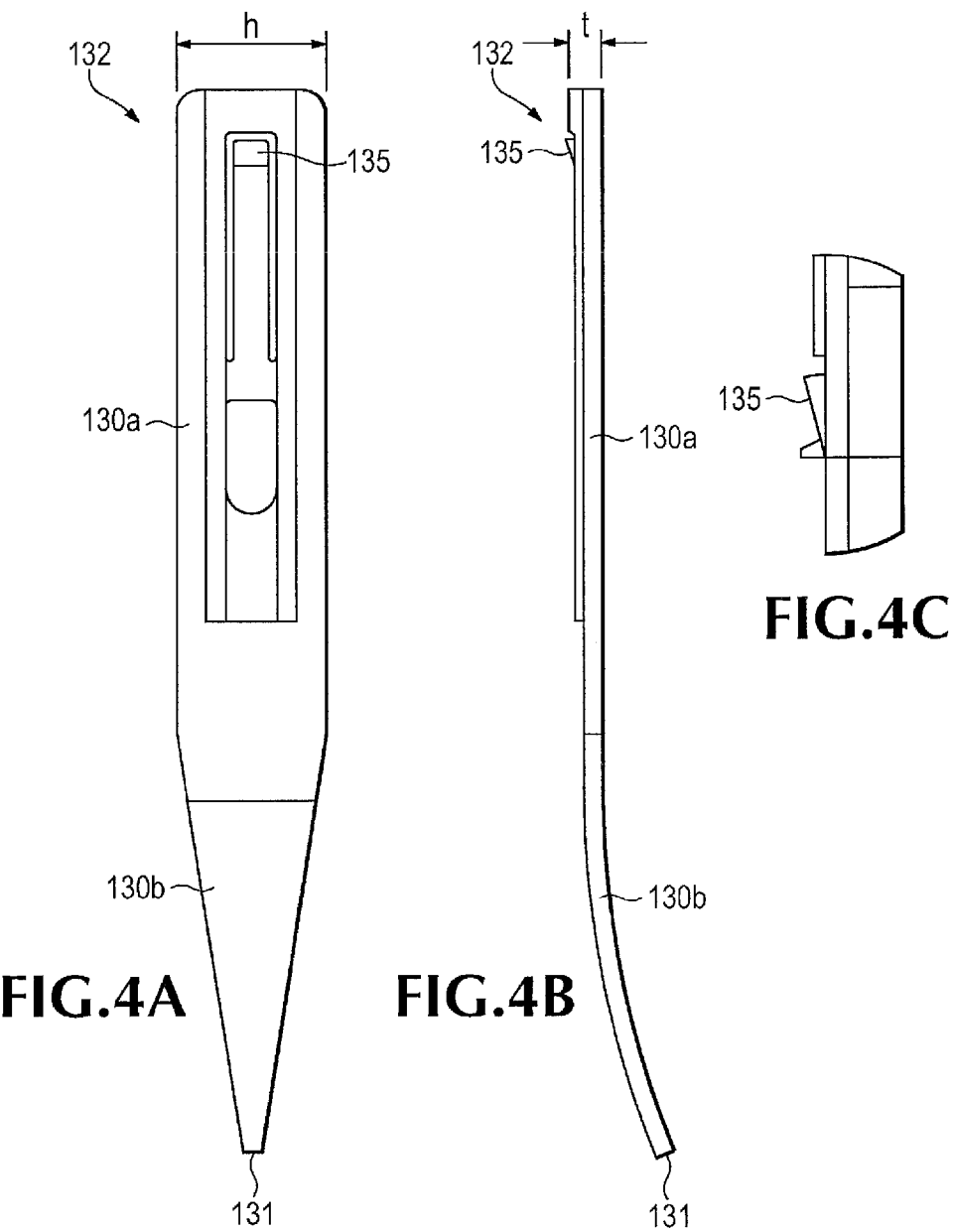

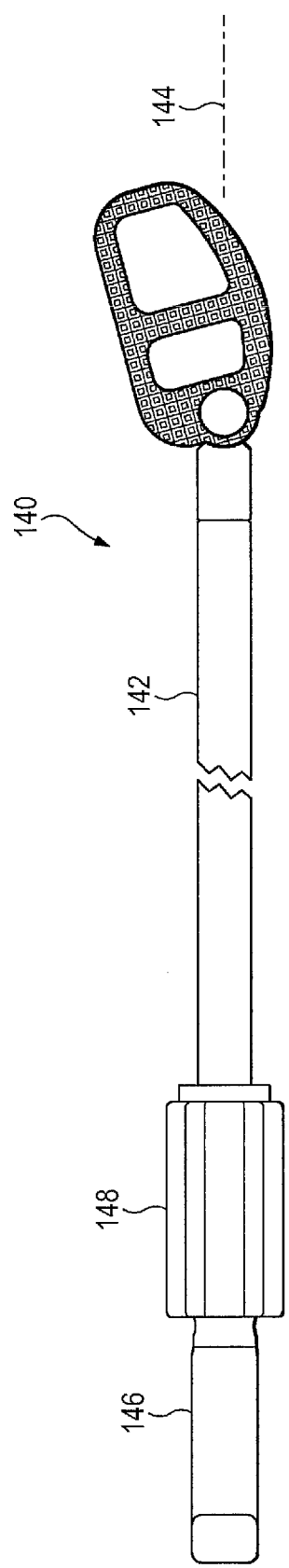

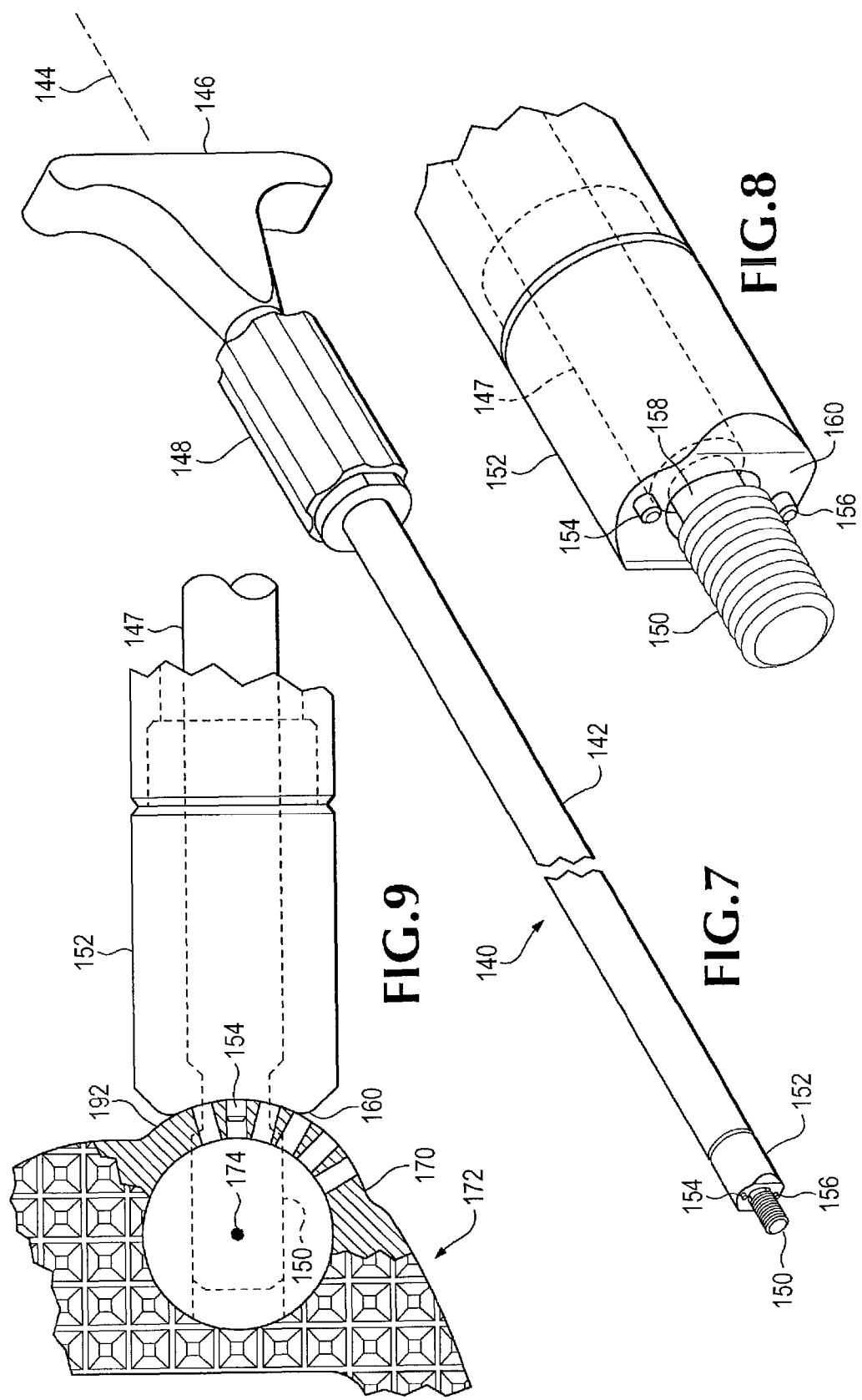

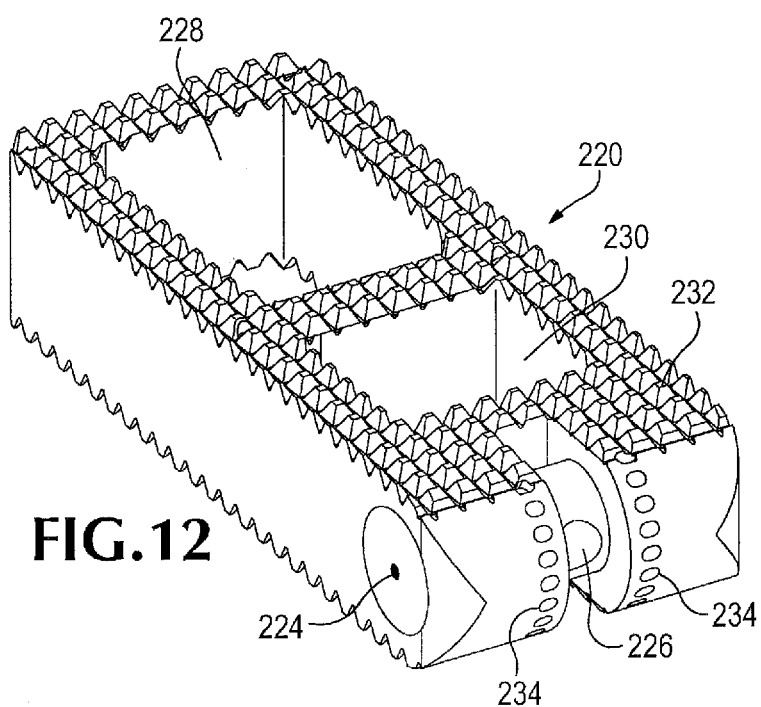

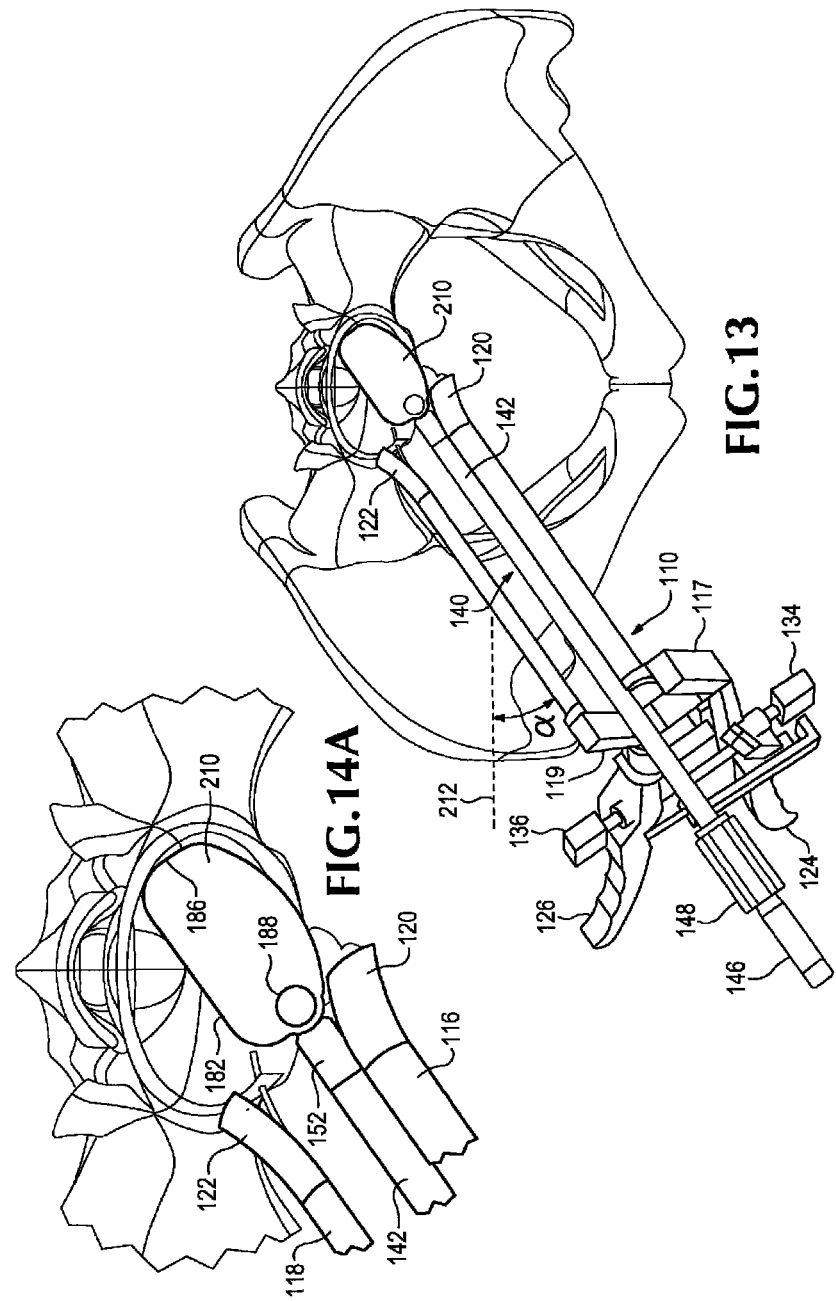

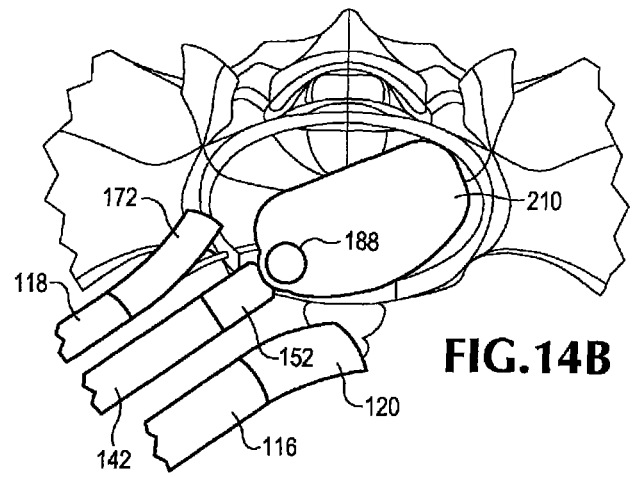
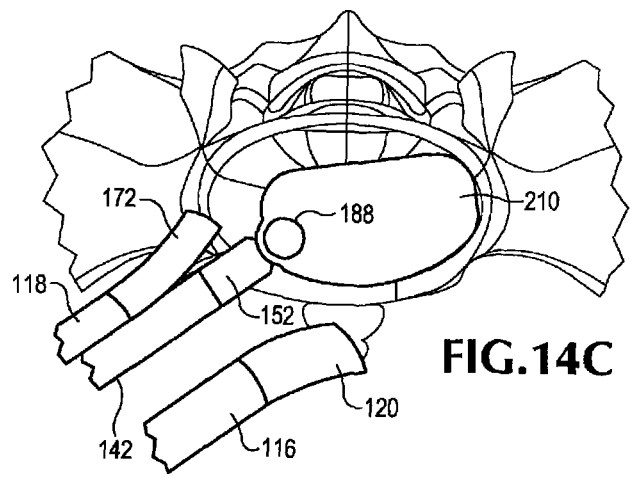

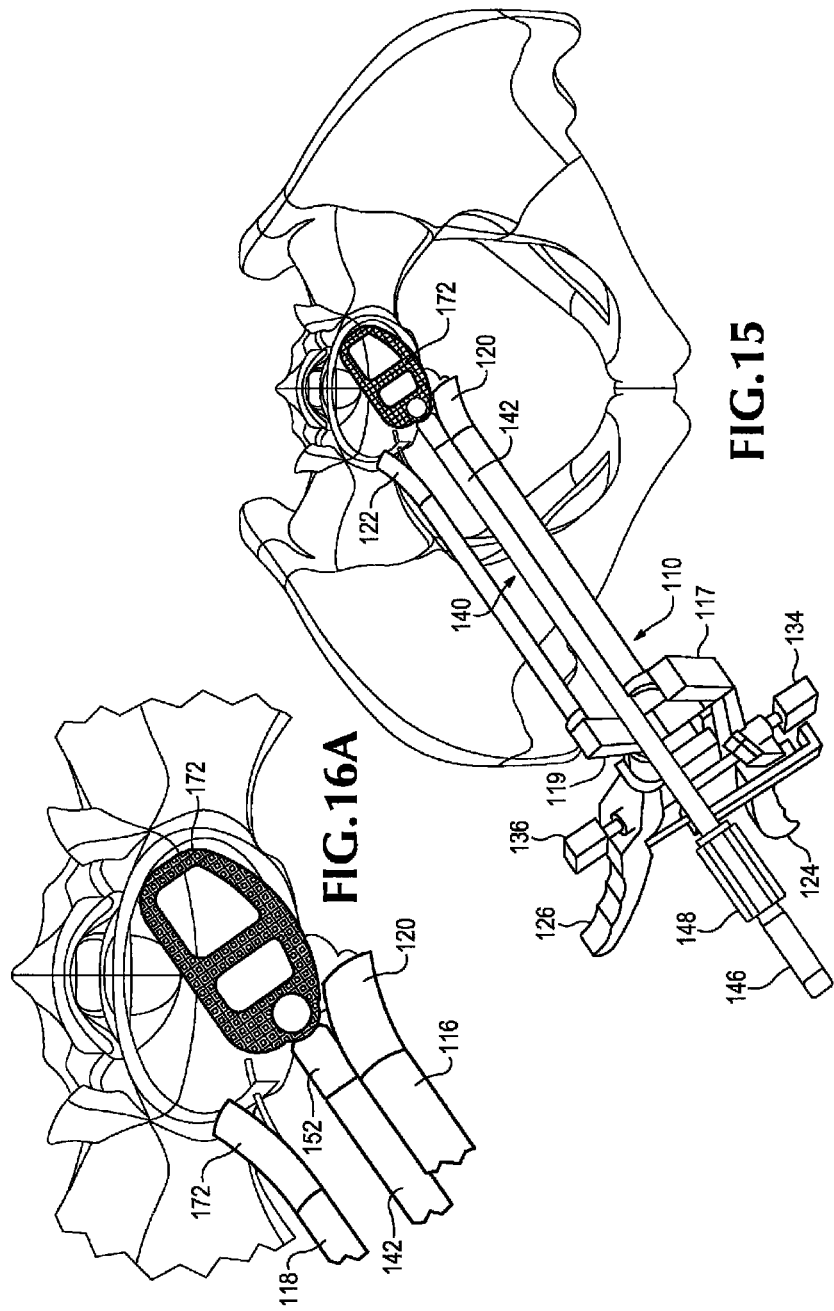

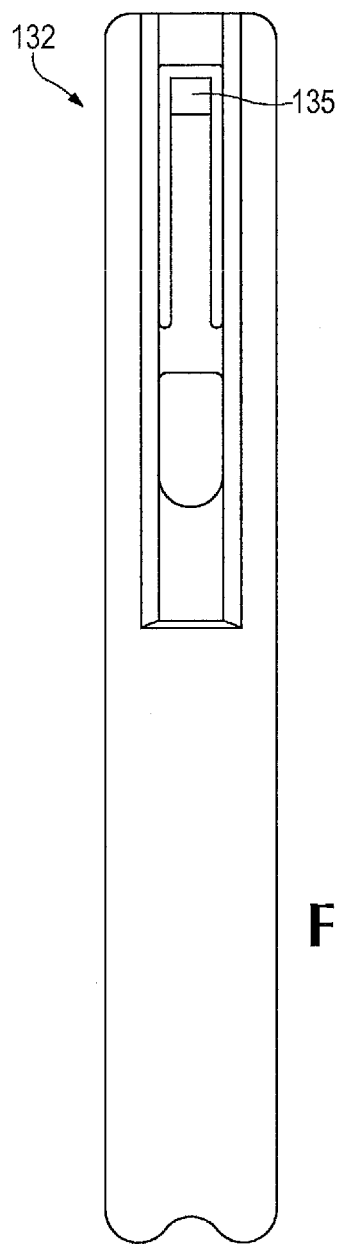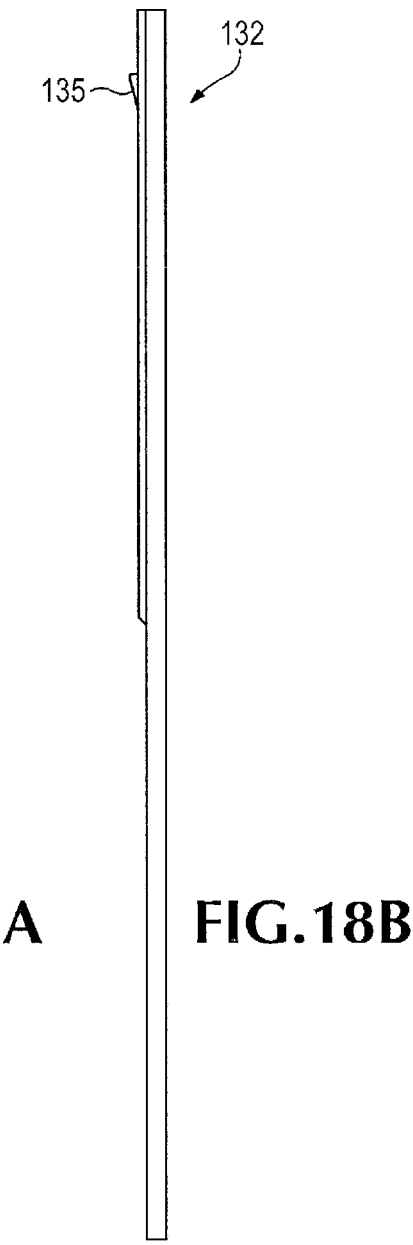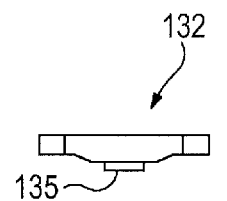
FIG.18A    FIG.18B
FIG.18C

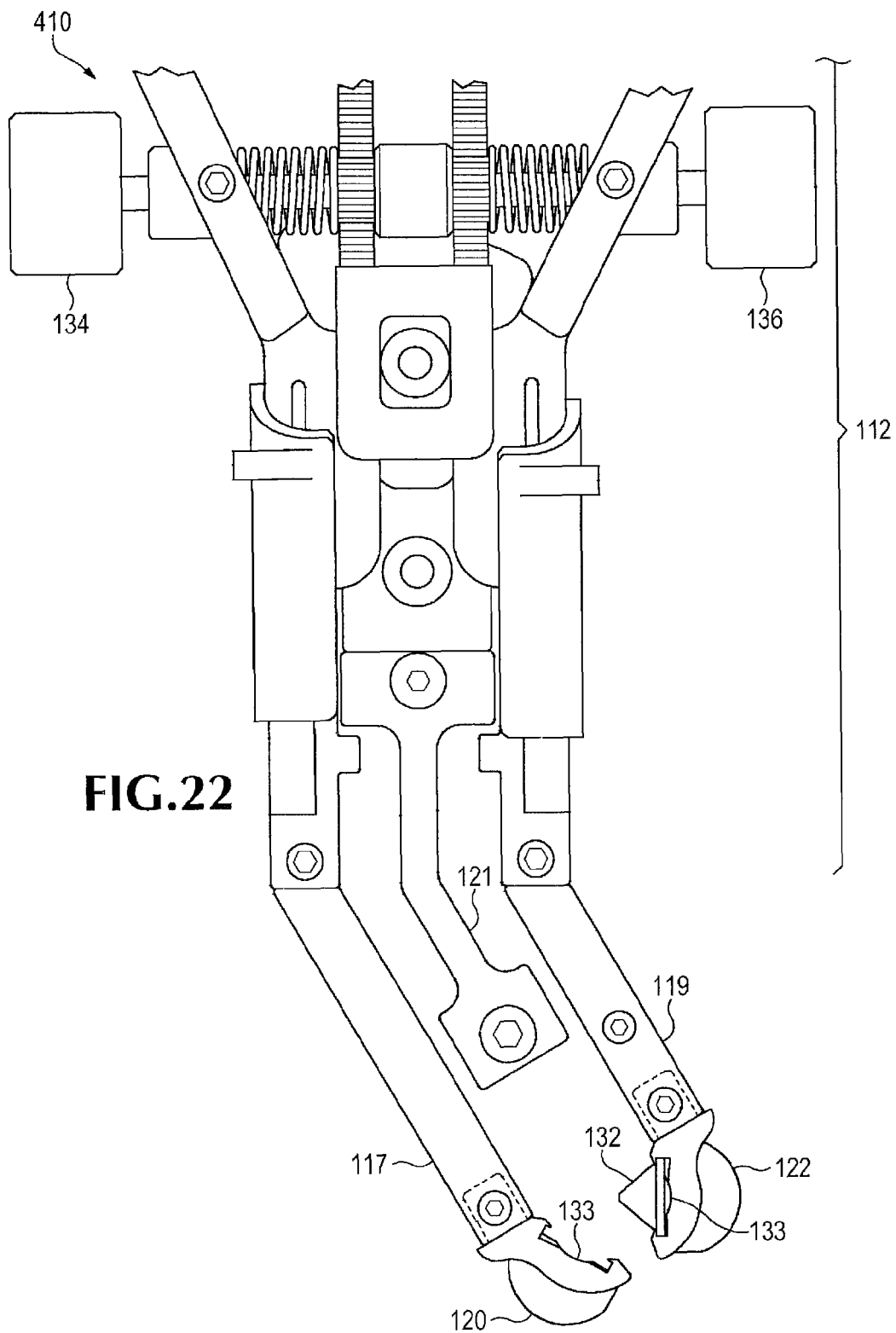

METHOD OF RETROPERITONEAL LATERAL INSERTION OF SPINAL IMPLANTS

PRIORITY CLAIM

This application is a Continuation of U.S. patent application Ser. No. 13/133,909 entitled "MINIMALLY-INVASIVE RETROPERITONEAL LATERAL APPROACH FOR SPINAL SURGERY" filed on Jun. 9, 2011, which was the National Stage of International Application No. PCT/US2009/069476, filed Dec. 23, 2009, which claims priority to U.S. Provisional Patent Application No. 61/140,926, filed Dec. 26, 2008, and U.S. Provisional Application No. 61/178,315, filed May 14, 2009, all of which are incorporated herein by reference.

BACKGROUND OF THE INVENTION

1. Field of the Invention

Spinal surgery methods and devices are disclosed for repairing damaged or deteriorated vertebrae at the lower lumbar levels, such as in the L5-S1 intervertebral space.

2. Description of the Relevant Art

The vertebral column is the central pillar of the body. It is a generally flexible column that bears tensile and compressive loads, permits bending motions, and provides an attachment site for ribs, muscles and other structures. The vertebral column includes irregular bones called vertebrae that are separated by fibrocartilaginous structures known as intervertebral discs. There are seven vertebral, twelve thoracic, five lumbar, five sacral, and four coccygeal vertebrae. A typical vertebra consists of a rounded anterior body and a posterior vertebral arch that together form a protective structure around the vertebral canal that contains the spinal cord.

The intervertebral discs can be damaged or undergo degeneration, which often results in painful and sometimes debilitating nerve impingement syndromes. It is sometimes necessary to surgically replace the native disc with prosthetic disc implants to relieve the pain, restore the functional mechanics of the vertebral column, and promote fusion between adjacent vertebral bodies. Procedures such as total disc arthroplasty (disc replacement) have used a direct anterior approach orthogonal to the midline of the vertebral body, but such procedures require unfettered anterior spinal exposure for precise midline placement of the prosthetic disc. The major vascular structures that run along the anterior spine must be mobilized to achieve this exposure, which typically requires the assistance of a vascular surgeon. The procedure also causes significant surgical disruption of the anterior annular element around the disc.

Bertagnoli has described an anterolateral transpsoatic approach (ALPA) for implantation of prosthetic disc replacement devices. The patient is positioned in a supine position on the operating table, with the arms in abduction. The target disc level is localized through bi-planar fluoroscopy, and an inflatable bladder is placed beneath the level of interest to permit additional lordosis. An anterolateral incision is made on the left side for access to lumbar intervertebral spaces, while the incision is made on the right side for access to L5-S1. The fascia of the external oblique muscle is opened along the direction of its fibers and the muscle is split. The retroperitoneal space is entered and the peritoneal sac mobilized away from the overlying fascia to develop an operative pathway along the anterior aspect of the psoas muscle to the lateral aspect of the intervertebral space. The target zone for annulotomy is from the one o'clock to three o'clock position above the L5-S1 level, which leaves the anterior longitudinal ligament intact and avoids mobilizing the iliac vessels. At the L5-S1 level the target annulotomy zone is from the eight o'clock to ten o'clock position with mobilization of the iliac vessel toward the midline. Injury to the left iliac vessel is an unfortunate complication of such procedures. Additional information about anterolateral approaches to spinal surgery at the L4-L5 level is found in Bertognali et al, U.S. Pat. No. 7,326,216.

A minimally invasive procedure promoted by Nuvasive, Inc. uses a direct lateral, retroperitoneal approach to access the intervertebral discs above the L5-S1 level with minimal muscular disruption. The patient is placed in a lateral decubitus position and the direct lateral incision is made in the axillary line. Another incision is made posterior to the lateral border of the erector spinae muscle, and finger dissection is conducted through this opening to the retroperitoneal space. The index finger of the surgeon sweeps the peritoneum anteriorly and palpates the psoas muscle. A dilator instrument is then introduced through the direct lateral incision and the index finger then guides the dilator instrument to the psoas muscle. The fibers of the psoas muscle are then split using blunt dissection and EMG monitoring to minimize damage to the nerves of the lumbar plexus that run through the posterior psoas muscle. A tissue distraction and tissue retraction assembly are then used to help establish an operative corridor to the direct lateral aspect of the intervertebral space at about the 3 o'clock position, as shown in U.S. Pat. No. 7,207,949. The direct lateral retroperitoneal approach to the L5-S1 space has not been possible because the anterior superior iliac spine obstructs a direct lateral approach to the L5-S1 intervertebral space. Hence approaches to the L5-S1 space typically use a standard anterior approach. For a laterally positioned patient, an extremely large sigmoidal incision has been required, with subsequent reflection of all the overlying musculature to expose the L5-S1 space.

It would therefore be useful to provide a minimally invasive approach to the L5-S1 space that minimizes injury to the blood vessels and nerves around the vertebral bodies. It would also be helpful to perform such a procedure in a manner that minimizes retroperitoneal scarring and damage to other body structures. Minimally invasive surgical approaches to the intervertebral spaces in the past have also been limited by the need to insert the prosthetic disc implant either into the front portion, posterior portion, or the side of the disc space to achieve stable placement of the prosthetic implant. It would therefore be useful to have a procedure that could avoid such a limitation at any vertebral level.

SUMMARY OF THE INVENTION

The inventor has found it is advantageous to provide a method, device and system that permit an angle between a disc implant and insertion instrument to be altered without removing the implant from the intervertebral space. This new surgical approach also removes the native disc contents from a generally lateral direction, which permits the periotoneal contents to fall out of the surgical field, while also taking advantage of the mechanics of anterior interbody surgery.

Disclosed methods, devices and systems are suitable for performing a minimally-invasive procedure for accessing the intervertebral space along an oblique pathway with an insertion instrument that holds a disc implant, and reorienting the angular relationship between instrument and implant while the implant is inside the body (for example at or within the disc space). In some disclosed embodiments, a prosthetic disc implant is inserted diagonally within the disc space, and the implant is then pivoted to a medial-lateral orientation within the disc space. The invention is particularly useful for accessing the L5-S1 intervertebral space along an anterolateral pathway to the anterior aspect of the spine, placing a prosthetic disc implant diagonally within the intervertebral space, and pivoting the implant within the disc space. However the method can also be used at other vertebral levels. In one embodiment, the oblique pathway has a caudal or cephalad-directed component, and the implant can be repositioned into a transverse anatomic plane through the intervertebral space.

In one embodiment, an implant is positioned in the intervertebral disc space of a laterally positioned subject by accessing the anterior face of the spinal disc intervertebral space, between the L5 and S1 vertebrae, from an anterolateral retroperitoneal approach. An oblique operative corridor is then established to the anterior face of the spinal disc space by introducing a retractor instrument anterolaterally to the spinal disc space, for example anterior to the anterior superior iliac spine, and in some instances between the level of the anterior superior iliac spine and the anterior inferior iliac spine. The spinal disc contents are removed from the intervertebral space through the operative corridor, and an elongated implant is introduced through the operative corridor into the intervertebral space diagonally (at an angle). The elongated implant is then pivoted within the intervertebral space to eventually position the implant substantially medial-laterally within the intervertebral space and achieve midline symmetric distribution of the mechanical load on the implant. The ability to pivot the implant within the intervertebral space permits the elongated implant to be generally aligned with the insertion instrument and advanced into the body through a relatively narrow operative corridor, then turned to its final position within the intervertebral space.

In a disclosed embodiment, the retractor instrument includes a proximal handle portion and a distal retractor blade portion that carries opposing ipsilateral and contralateral vascular retractor blades that are placed between the right and left iliac vessels and moved apart from one another to retract the right and left iliac vessels away from the anterior face of the spinal disc intervertebral space. A particular example of the retractor instrument has an ipsilateral arm on which the ipsilateral blade is mounted and a contralateral arm on which the contralateral blade is mounted. The retractor blades are placed between the right and left iliac vessels to move them away from one another to expose the anterior surface of the spine as the ipsilateral and contralateral arms of the retractor instrument move the retractor blades apart. For example, the blades of the retractor instrument are positioned at the anterior face of the vertebral body adjacent the anterior longitudinal ligament, and the retractor blades are spread to expose an area from about the 10 o'clock to 2 o'clock position of the vertebral body.

The elongated implant may be advanced into the intervertebral space through the operative corridor defined by the arms of the retractor instrument by securing the implant to a distal end of an elongated rigid introducer instrument and advancing the implant on the introducer instrument through the operative corridor to the anterior face of the intervertebral space at an oblique angle so that the implant enters the disc space diagonally. The angle between the implant and the introducer is then selectively changed to pivot the implant in one or more subsequent steps into the medial-lateral position for symmetric midline placement within the intervertebral space. In some embodiments the introducer instrument has a distal docking element that selectively docks with an interface element of the implant in a series of preselected positions to alter the angle between the implant and the introducer instrument. For example, the docking element is a plurality of docking pins on the tip of the introducer element, and the interface element is a corresponding series of docking holes that cooperatively mate to hold the implant in preselected angular orientations to the introducer instrument.

In some disclosed embodiments, the implant is an elongated elastomeric member that has a top bearing face, a bottom bearing face, a front face, a rear face, an ipsilateral face and a contralateral face. The rear face of the implant may be substantially flat. The contralateral face of the implant may be rounded (particularly at its corners that adjoin the front and rear faces) to minimize trauma induced by advancing the implant diagonally into the intervertebral space at the oblique angle, and using the ipsilateral face to function as an impact hinge or pivot point as the implant is moved in one or more realignments from the oblique to medial-lateral orientation. The ipsilateral end of the implant may have a pivot axis and an interface element, such as multiple pairs of spaced docking holes arranged on a curved surface that extends partially circumferentially around the pivot axis. The selected pairs of spaced docking holes are positioned to mate with the docking element of the introducer instrument, such as a pair of docking pins that extend from a distal tip of the introducer instrument.

In some embodiments the implant tapers in height from its front face to rear face, and/or medially to laterally, and it may be a partially hollow member in which the top face and bottom face are substantially open and separated by an internal divider wall that extends from the front face to the rear face to form a contralateral and ipsilateral window though the implant to promote the growth of bone within the implant. In some disclosed embodiments, the implant is a slightly compressible member in which the front face is convex and the ipsilateral face includes the interface element that mates with the docking element. The external surfaces of the implant (such as the top and bottom faces of the implant) have protuberances that help frictionally engage the implant to adjoining vertebral bodies, and also promote bone growth into the implant. The protuberances may have a variety of shapes, such as grooves or corrugations, but a frustopyramidal protuberance is believed to be particularly suitable.

The retractor instrument may also take a variety of forms, but certain disclosed embodiments have an ipsilateral arm that is shorter than the contralateral arm. A retractor blade on the ipsilateral arm therefore extends a shorter distance from the handle than the retractor blade on the contralateral arm. This asymmetric arrangement permits the retractor instrument to be advanced diagonally through the body from an anterolateral entrance point through the abdominal wall to the anterior aspect of the vertebral body. Since the contralateral arm is longer than the ipsilateral arm, the retractor blades at the anterior vertebral body span the anterior face of the vertebral body, for example from the 10 o'clock to 2 o'clock positions. The retractor blades may be curved outwardly from a longitudinal axis of the retractor instrument to help minimize damage to the blood vessels as they are retracted. A thin shim with a tapered tip may be inserted into the intervertebral space and mounted to the ipsilateral blade to retain the instrument in its desired angular orientation and distract adjacent vertebral bodies (such as L5 and S1) apart from one another during the procedure. The shim curves inwardly into the disc space, toward the midline of the body, away from the ipsilateral retractor blade, and toward a longitudinal axis of the retractor instrument. The shim has a height sufficient to maintain the adjacent vertebral bodies spaced from one another while a trial spacer and subsequent disc implant are pivoted into place within the disc space. The present disclosure also includes a system for positioning an implant in an intervertebral space of a subject. In certain disclosed embodiments, the system includes the retractor instrument for establishing an operative corridor to the anterior face of the intervertebral space. The retractor instrument has a proximal handle portion and a distal retractor blade portion that includes opposing ipsilateral and contralateral arms that are movable toward and away from one another to define a portion of the operative corridor therebetween. In certain embodiments, the ipsilateral retractor blade is carried by the ipsilateral arm, and a contralateral vascular retractor blade is carried by the contralateral arm. The contralateral arm and blade are longer than the ipsilateral arm and blade so that the retractor instrument can be introduced at an oblique angle with the two retractor blades spaced apart on the anterior aspect of the vertebral body.

The system also includes the introducer instrument for advancing an elongated prosthetic spinal disc implant between the arms and blades of the retractor instrument to the intervertebral space at an oblique angle so that the implant enters the intervertebral space diagonally. The introducer instrument is capable of pivoting the implant in the intervertebral space, for example by connecting docking pins on a tip of the introducer instrument to different sets of corresponding docking holes on the implant. The docking pins selectively mate with the different sets of docking holes on the implant to maintain the implant at different fixed angles to the introducer instrument. By mating the docking pins with different docking holes, the implant can be pivoted within the intervertebral space to move it from its initial diagonal orientation to a medial-lateral orientation generally symmetric with respect to the axis of the vertebral column. In certain embodiments, the system also includes the implant which has a top bearing face, a bottom bearing face, a front face, a rear face, an ipsilateral face and a contralateral face. The implant's contralateral face may be rounded to minimize trauma induced by advancing the implant diagonally into the intervertebral space and pivoting it around a pivot axis within the intervertebral space. The implant has an interface element for coupling with the introducer instrument and pivoting the implant within the disc space. For example, the interface element includes multiple pairs of spaced docking holes arranged on a curved surface that extends partially circumferentially around the pivot axis, and selected pairs of spaced docking holes are positioned to mate with the docking element of the introducer instrument. In certain disclosed embodiments, the implant tapers in height from the front face to the rear face. The implant may also be a partially hollow member in which the top face and bottom face are substantially open and may be separated by an internal divider wall that extends from the front face to the rear face to define the ipsilateral and contralateral windows therebetween for promoting tissue growth within the implant.

Another aspect of the invention is the prosthetic implant itself, the retractor itself, and the introducer element itself.

BRIEF DESCRIPTION OF THE DRAWINGS

Advantages of the present invention will become apparent to those skilled in the art with the benefit of the following detailed description of embodiments and upon reference to the accompanying drawings in which:

FIG. 2B is an isolated perspective view illustrating the components and use of an initial distraction assembly that includes a K-wire, an initial dilating cannula with handle, and a split-dilator housed within the initial dilating cannula;

FIG. 2C is an isolated perspective view illustrating the K-wire and split-dilator of the initial distraction assembly with the initial dilating cannula and handle removed;

FIG. 4A is a front elevation view of a shim for placement on the ipsilateral blade of the retractor instrument;

FIG. 4B is a side view of the shim of FIG. 4A;

FIG. 4C is a top view of the shim of FIGS. 4A and 4B;

FIG. 6 is a perspective view of an introducer instrument for guiding an implant to a spinal disc space, showing the implant connected to the introducer instrument for movement about a pivot axis;

FIG. 7 is an isolated perspective view of the introducer instrument;

FIG. 8 is an enlarged, fragmentary view of the tip of the introducer instrument of FIG. 7 illustrating the instrument interface of the implant, and showing the pins on the distal tip of the instrument for connection to positioning holes on the implant;

FIG. 9 is an enlarged, fragmentary view of the implant held in a fixed angular position relative to the introducer element by the pins of the instrument interface locked into a preselected set of positioning holes on the implant;

FIG. 12 is a perspective view of a second embodiment of the implant;

FIG. 13 is a schematic top perspective view of the pelvis with a retractor instrument introduced obliquely into the subject's body along an anterolateral operative trajectory, and with the introducer instrument advanced through the operative corridor defined by the retractor instrument. A trial spacer is attached to the distal end of the introducer instrument for introduction diagonally into the L5-S1 intervertebral space;

FIG. 14A is an enlarged top view of the L5-S1 disc space shown in FIG. 13, illustrating the rounded contralateral face of the trial spacer impacting the far lateral aspect of the apophyseal ring;

FIG. 14B is a view similar to FIG. 14A, but illustrating adjustment of the angle between the introducer instrument and the body of the trial spacer by repositioning the pins on the tip of the instrument in a different set of pin receiving holes on the trial spacer;

FIG. 14C is a view similar to FIG. 14C, but illustrating progressive reorientation of the trial spacer in a generally medial-lateral orientation within the intervertebral space;

FIG. 15 is a view similar to FIG. 13, but showing a subsequent step of the procedure in which the introducer instrument has advanced an implant to the disc space;

FIGS. 16A, 16B and 16C are top views of the L5-S1 disc space, illustrating progressive reorientation of the implant within the disc space by repositioning of the pins on the tip of the introducer instrument in different sets of pin receiving holes on the implant;

FIG. 18A is a front elevation view of a shim for placement on the ipsilateral blade of the retractor instrument;

FIG. 18B is a side view of the shim of FIG. 18A;

FIG. 18C is a top view of the shim of FIGS. 4A and 4B;

FIG. 22 is a top view of the retraction instrument of FIG. 21, showing a mechanism for moving the retractor blades;

Figure 1A:
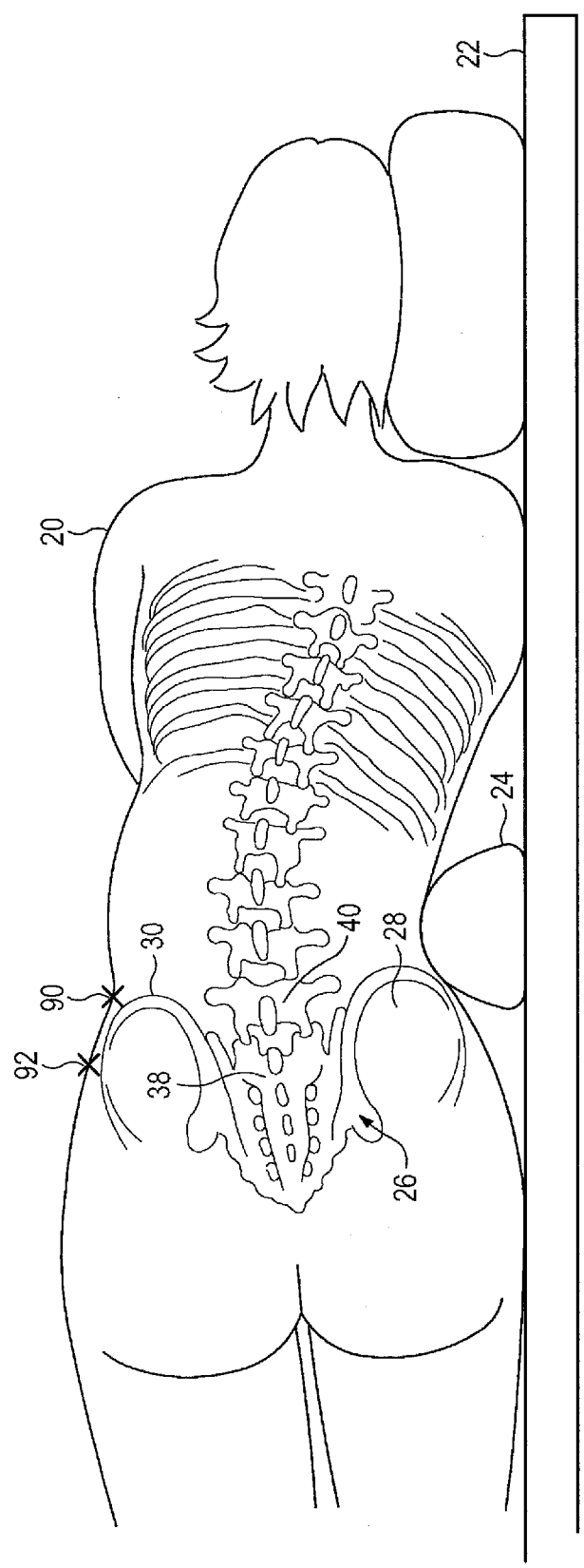
FIG. 1A illustrates a patient positioned in a right lateral decubitis position for minimally-invasive spinal surgery using a retroperitoneal approach.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary.

It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Embodiments of the invention are disclosed herein for accessing an intervertebral space, such as the L5-S1 space, and implanting a prosthetic disc implant within that space. The disclosed devices, methods and systems are suitable for use in a minimally invasive procedure for repairing degenerated or otherwise injured intervertebral discs.

General Overview of the Surgical Procedure

The method generally includes initially accessing the intervertebral space using a retroperitoneal lateral approach. Then, with a finger-directed dilator or other suitable instrument, the distal retroperitoneum is swept anteriorly to expose an eventual channel to a direct approach to L5-S1. In most people, the direct approach to L5-S1 is anterior to the anterior superior iliac spine, or between the anterior superior iliac spine and the anterior inferior iliac spine. An incision is then made to open this channel, and blunt dilators are directed in an oblique direction directly to the mid-anterior aspect of L5-S1, for example between the 10 o'clock and 2 o'clock position. Fluoroscopic guidance may be used in accordance with known techniques to assist in advancing and positioning the dilators.

A retractor is then advanced over the dilators. In certain embodiments, the blades of the retractor are translucent so that the retracted contents can be seen through the blades. In contrast to existing retractors used in minimally invasive spinal surgery, the blades are shaped so that the curvature of the retractor blades conforms to the unique shape of the anatomy for the approach described herein, and is particularly suitable for use in this portion of the spine. For example, the ipsilateral blade may be shorter than the contralateral blade, and the ipsilateral blade may be more arcuate with a steeper curve as compared to the less curved, straighter contralateral blade. In one embodiment, the blades can accommodate a xenon light source for visualization in the cavity.

Once the retraction blades are advanced to the anterior aspect of the spine (for example between the 10 o'clock and 2 o'clock positions at the L5-S1 intervertebral space), the retractor blades are positioned below the iliac bifurcation between the right and left iliac vessels. The retractor blades are moved apart to increase exposure of the anterior vertebral column. A docking shim that is angled away from the ipsilateral blade and toward the disk space is placed in the intervertebral space to secure the retractor in position and maintain distraction of the vertebral bodies. If the small middle sacral artery is viewable in the midline, the surgeon may choose to ligate or electrocauterize this small vessel.

The procedure provides a relatively large window within which a discectomy and reconstruction can be carried out. The tools used for the discectomy may be slightly angled (relative to tools used for existing techniques) to maximize disc removal from an oblique direction. Trial spacers and final disc implants have a unique design suited to the trajectory of the implantation, as described in greater detail below. Radiopaque markers may be included on the trial spacers and implants (for example at its corners) to enable the structures to be visualized under fluoroscopy.

One or more trial spacers are then introduced into the evacuated disc space to help select an appropriate size implant. During introduction of the trial spacer or final implant, the initial insertion trajectory is oblique, resulting in diagonal entry of the trial spacer into disc space with impaction of the contralateral face of the implant or trial spacer to the far lateral aspect of the apophyseal rings (for example of L5-S1). The angle of impaction is then reoriented so that the portion of the trial spacer or implant that is present in the more anterior portion of the intervertebral space is impacted posteriorly on the apophyseal ring by using the contralateral side as a swivel point. Under fluoroscopic control, final seating of the implant or trial spacer is achieved. Once the final implant is in place, retraction is slowly released by allowing the retraction blades to move toward one another to check for any residual bleeding. The retractor is then slowly removed so that the skin closure of the percutaneous incision can be carried out.

This general summary of the procedure is illustrated in more detail in the following sections of this specification.

Positioning the Patient and Relevant Spinal Anatomy

Figure 5A:
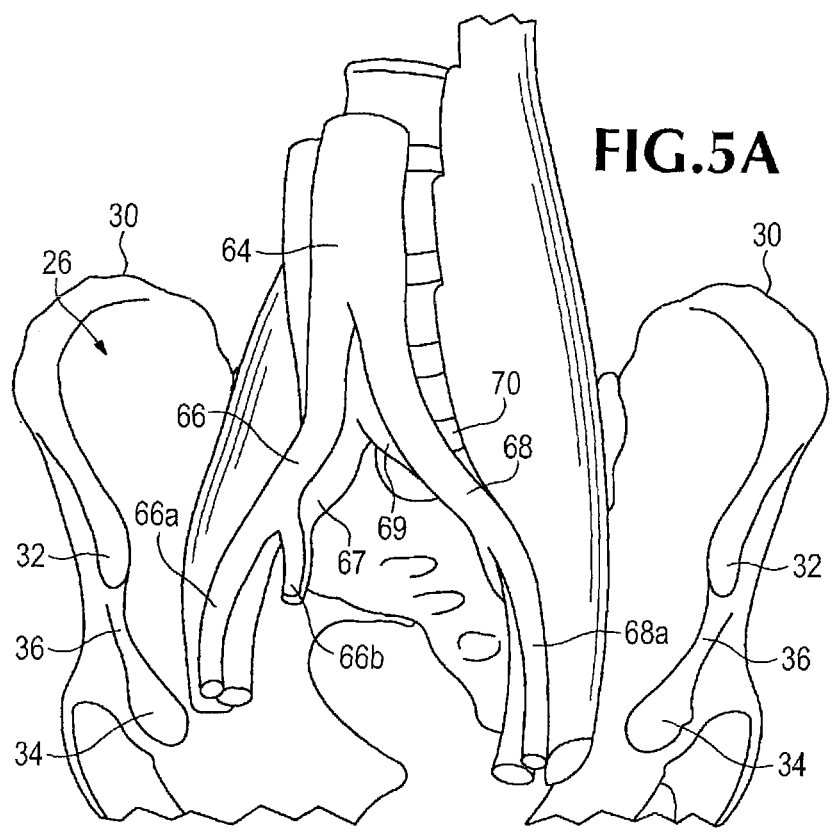
FIG. 5A is a perspective fragmentary view of the pelvis and the sacro-lumbar segment of the spinal column illustrating the bifurcation of the iliac vasculature along the anterior aspect of the spinal column.
Figure 5B:
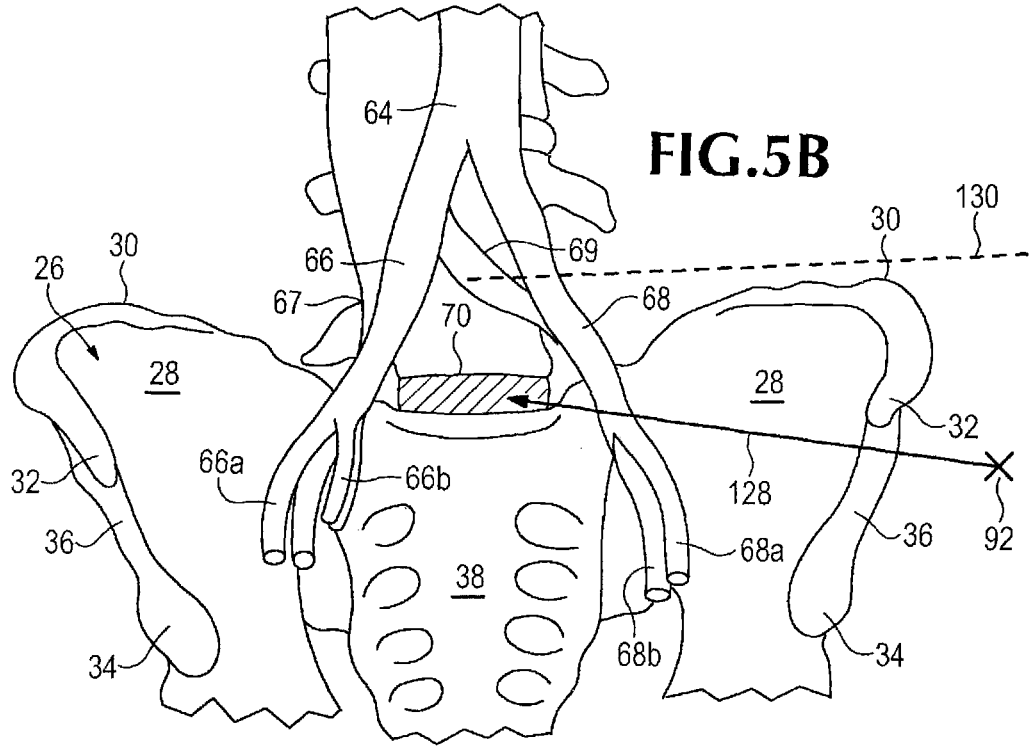
FIG. 5B is a front view of FIG. 5A with the iliac vessels retracted to expose the L5-S1 disc space.

As shown in FIG. 1A, a patient 20 is placed in a direct right lateral decubitis position with the patient's right side down on an operating table 22 and the left side up. A bolster pillow 24 is placed at the waist of patient 20 to bend the body at that point, which elevates and tilts the pelvis 26 of patient 20. Pelvis 26 is schematically shown in FIGS. 1, 5A and 5B to include an ileum 28, with an iliac crest 30, anterior superior iliac spine 32, and anterior inferior iliac spine 34. A notch 36 (FIGS. 5A and 5B) is formed between the superior and inferior iliac spines 32, 34. The spinal anatomy is schematically illustrated in FIG. 1A, wherein the sacrum 38 is shown connected to the L5 vertebra 40. Higher levels of lumbar and thoracic vertebrae are shown superior to the L5 disc. The anatomy of the L5 vertebra is illustrated in more detail in FIG. 1B, wherein the vertebra includes an anterior vertebral body 42 and a posterior vertebral arch 44 that cooperatively define spinal foramen 46. Vertebral body 42 includes a circumferential apophyseal ring 48, while vertebral arch 44 includes a spinous process 50, right transverse process 52 and left transverse process 54. Positions around vertebral body 42 can be designated arbitrarily by hours of the clock, with anterior-most position 56 designated the twelve o'clock position. Hence an anterior face of vertebral body 42 is designated herein as the face 58 that extends from about the ten o'clock position 60 to the two o'clock position 62. The axis of the vertebral column is located generally at the center of vertebral body 42.

Figure 1C:
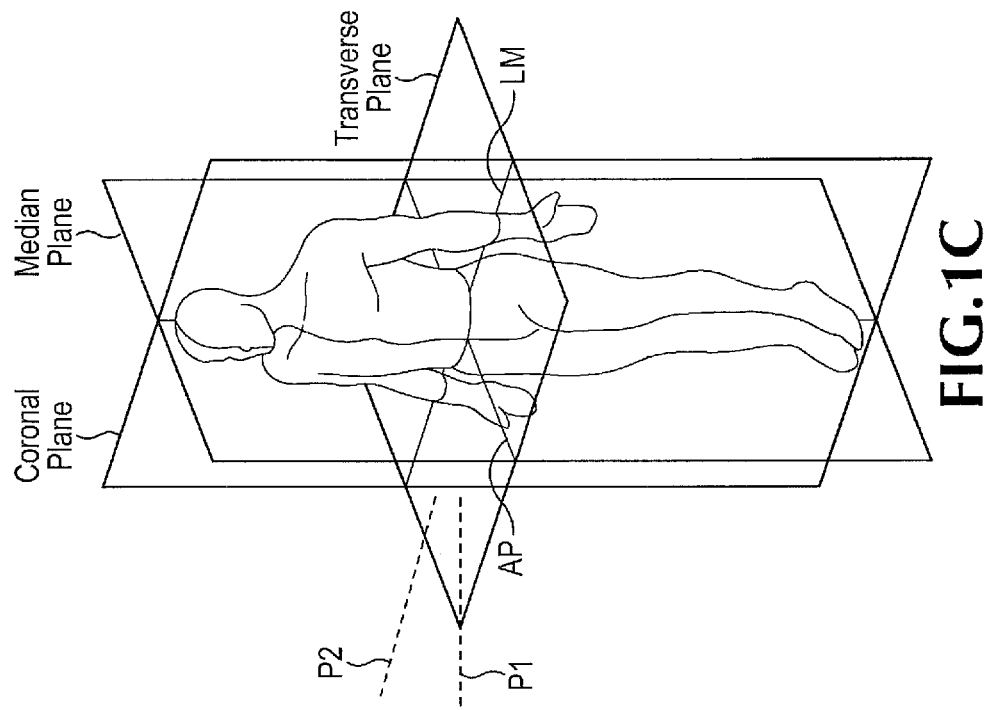
FIG. 1C is a schematic perspective view of the human body illustrating several anatomic reference planes.
Figure 1B:
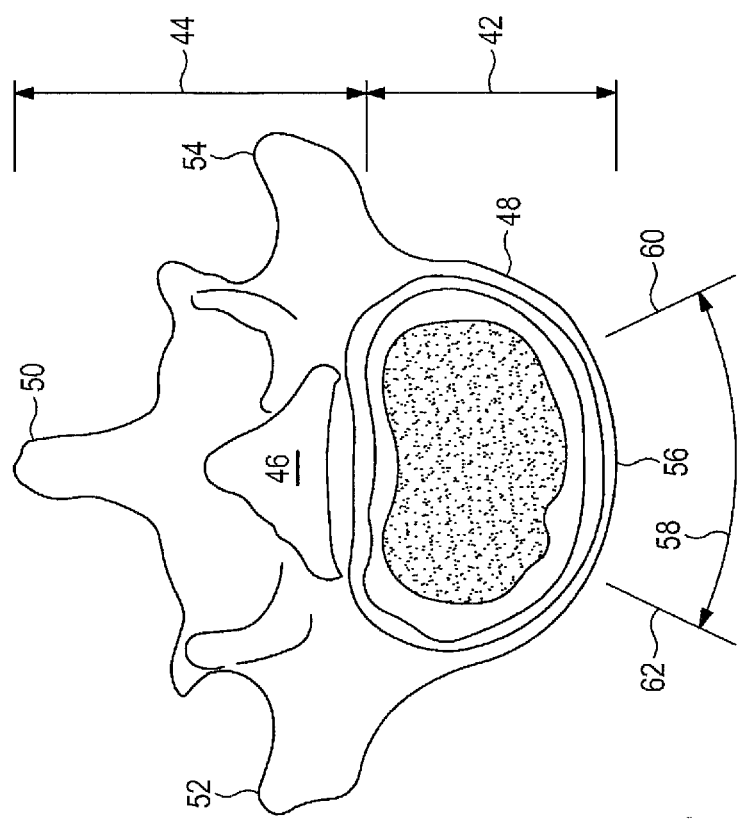
FIG. 1B is a schematic top view illustrating the anatomy of the L5 vertebra.

To clarify some of the terms in this specification, the anatomic planes of the body in the standard anatomical position are shown in FIG. 1C. In general anatomic terminology, "superior" means closer to the head, "posterior" means closer to the posterior surface of the body, "anterior" means closer to the anterior surface of the body, "cephalad" means toward the head, "caudad" means toward the feet. The anatomic reference planes in FIG. 1C are the "coronal plane" that separates the body into anterior and posterior halves, and the "median plane" that separates the body into right and left parts. A transverse plane is shown, which is any plane that is perpendicular to the coronal and median planes; multiple transverse planes exist at different levels of the body. With reference to the coordinate planes of FIG. 1C, the "noon" position is on the front of the body along the A-P (anterior-posterior) line at which the median plane intersects a transverse plane. The three and six o'clock positions are along the L-M (lateral-medial) line at the intersection of the transverse and coronal planes.

An "oblique plane" is any plane that is at an angle (not within or parallel) to any one of the coronal, median or transverse planes. Hence an operative corridor is "oblique" if it is an oblique plane. An oblique angle can lie in one of the illustrated coronal, median or transverse planes, be parallel to one or two of those planes, or be outside of (and not parallel) to all three of them. For instance, an oblique pathway P1 to an intervertebral space can extend in a transverse plane at a non-zero angle to the median plane. Alternatively, an oblique pathway P2 can extend at a non-zero angle to the transverse, coronal and median planes.

Additional pertinent anatomy at the anterior aspect of the spine is illustrated in FIGS. 5A and 5B, which shows the aortic bifurcation 64 into the right and left common iliac arteries 66, 68, each of which divides into an external iliac artery 66a, 68a and an internal iliac artery 66b, 68b. Accompanying common iliac veins 67, 69 are also shown in FIG. 5A. The descending aortic artery, bifurcation 64, and the bifurcated iliac vessels are at the anterior face of the vertebral bodies, and have complicated surgical approaches that attempt to access the anterior vertebral body to repair a damaged spinal disc. The L5-S1 intervertebral space 70 is shown in FIG. 5A without retraction of the iliac vessels, and in FIG. 5B with retraction of the iliac vessels to expose L5-S1 intervertebral space 70.

Figure 2A:
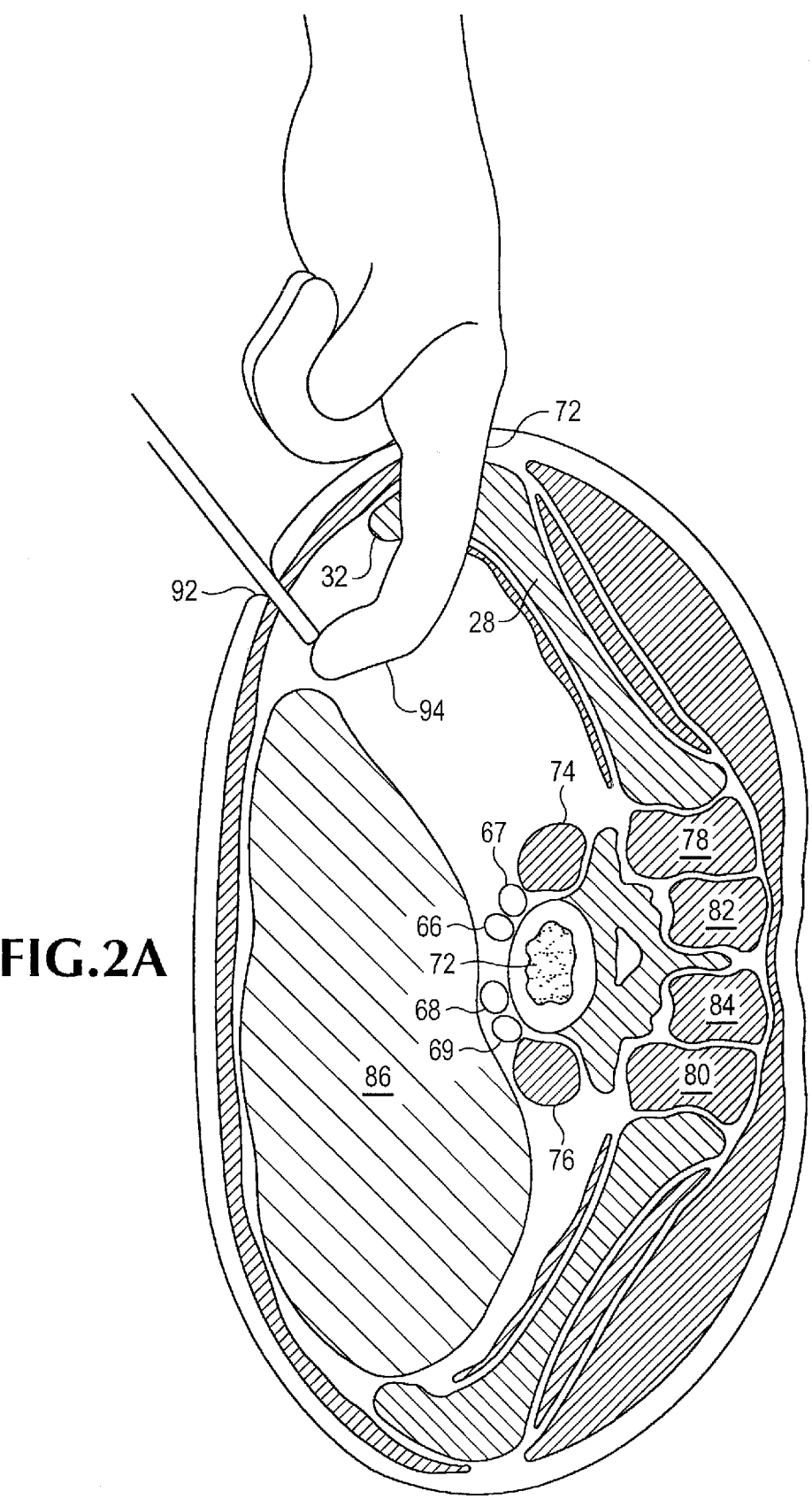
FIG. 2A is a schematic cross-sectional view of the abdomen at the level of the L5-S1 intervertebral space illustrating the left anterolateral displacement of the peritoneum and the right anterolateral introduction of a dilator through an incision toward the L5-S1 space under the guidance of a surgeon's finger introduced through a lateral incision.
Figures 3A, 3B:
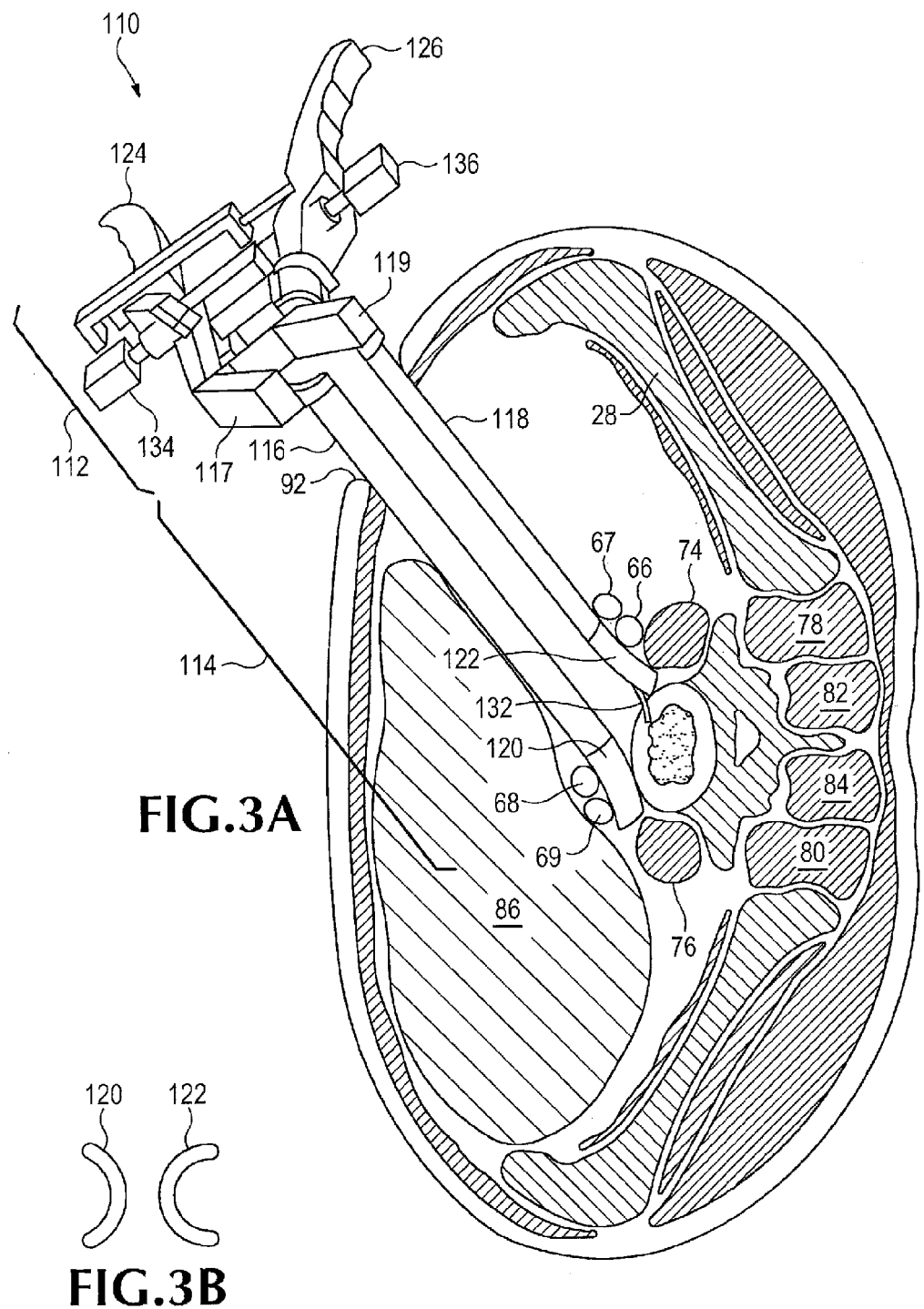
FIG. 3A is a view similar to FIG. 2A, but showing introduction of a minimally invasive retractor instrument through the right anterolateral incision, and its positioning at the L5-S1 intervertebral space with the right and left iliac vessels retracted away from the anterior spine.
FIG. 3B is an isolated schematic end view of the retractor blades on the retraction instrument, illustrating the greater curvature of the shorter retraction blade.

Additional pertinent perispinal anatomy is shown in FIGS. 2A and 3A, wherein right and left common iliac arteries 66, 68 and veins 67, 69 are shown in their normal anatomic position on the anterior aspect of the spine. The nucleus pulposus 72 of the L5-S1 intervertebral disc is illustrated, as are the right and left psoas muscles 74, 76, the right and left erector spinae muscles 78, 80 and the right and left transversospinalis muscles 82, 84. The peritoneum 86, which is normally adjacent and adherent to the retroperitoneal structures, is shown in FIGS. 2A and 3A after it has been moved anteriorly and separated from the retroperitoneal structures on the right side of the body to clear an operative pathway to the L5-S1 intervertebral space.

Access to Retroperitoneal Space and Establishing Operative Corridor to Intervertebral Space The surgeon palpates the subject to locate the position of the anterior superior iliac spine 32, and an initial incision 90 (FIG. 1) is made at this point in the mid-axillary line, as in a standard retroperitoneal approach. As shown in FIG. 2A, blunt finger dissection is directed caudally in the retroperitoneal plane to connect to a point that is parallel the L5-S1 disc space, just anterior to ileum 28. The surgeon's finger 94 sweeps peritoneum 86 anteriorly, moving it away from the ileum 28 and the retroperitoneal structures in the right side of the abdominal cavity. A second skin incision 92 (FIGS. 1A and 2A) is then made inferior to first incision 90. Second incision 92 is anterior to first incision 90, between the anterior axially line and the sheath of the rectus abdominis muscle, and is approximately 3-5 cm in length. Second incision 92 is made at the level of the L5-S1 disc space, which is determined fluoroscopically prior to making the incision. FIG. 2B illustrates an initial access assembly 100 for accessing the targeted intervertebral space, such as the L5-S1 intervertebral space. Although a particular device and method are described for accessing the L5-S1 intervertebral space, the disclosed invention is not limited to use of this particular device and method. The term "accessing" the intervertebral space or its face is meant to broadly include any device and/or method for establishing a pathway from a surface incision to the disc space or its face. Illustrated access assembly 100 includes a K-wire 102, an initial dilating cannula 104 with handle 106, and a split-dilator 108 housed within the initial dilating cannula 104. The entire assembly 100 is advanced under fluoroscopic guidance through the tissue towards the surgical target site (i.e. annulus). This may be accomplished using a nerve detection and/or direction device as described in U.S. Pat. No. 7,207,949, although the nerve detection capability is not necessary. Initial dilating assembly 100 is advanced until the distal ends of split-dilator 108 and initial dilator 104 are positioned within the disc space. The initial dilator 104 and handle 106 are then removed (FIG. 2C) to leave split-dilator 108 and K-wire 102 in place. Split-dilator 108 is thereafter split such that the respective halves 108a, 108b are separated from one another to distract tissue in a generally cephalad-caudal fashion relative to the target site as described in more detail in U.S. Pat. No. 7,207,949. Split dilator 108 may thereafter be relaxed (allowing the dilator halves 108a, 108b to come together) and rotated approximately 90 degrees such that the dilator halves 108a, 108b are disposed in a transverse anatomic plane. Once rotated in this manner, the dilator halves 108a, 108b are again separated to distract tissue in the transverse plane. Each dilator half 108a, 108b may be provided with one or more electrodes (preferably at their distal regions) equipped for use with a nerve surveillance system, such as, by way of example, the Neuro Vision System, although the nerve monitors are optional.

Progressively larger dilators (not shown) may be used to further establish the operative pathway. The dilators are labeled with depth markings to help assure insertion of the successive dilators to the appropriate depth. The dilators are introduced obliquely into the body along a diagonal pathway from incision 92 to the anterior aspect of the spine to enter the intervertebral space between the twelve o'clock and two o'clock positions. The particularly illustrated pathway is generally in a transverse plane at the level of L5-S1, but at an angle to (and between) the coronal and median planes (for example in the direction of the pathway P1 in FIG. 1C). However, the pathway can also be at an angle to the transverse plane as well (for example, at the same angle as pathway P2 in FIG. 1C). The dilator pathway helps determine the eventual operative corridor that is established by placement of retraction instrument 110. However, in some embodiments, the retraction instrument 110 can itself establish the operative corridor without the initial use of the dilators.

In the illustrated embodiment, one of more of the dilators is left in place to serve as a guide for insertion of a retractor instrument 110 (FIG. 3A). Retraction instrument 110 includes a proximal handle portion 112 and a distal retractor blade portion 114 that includes opposing contralateral retraction arm 116 and ipsilateral retraction arm 118, which respectively carry a terminal contralateral retraction blade 120 and ipsilateral retraction blade 122. Each of blades 120, 122 is curved longitudinally away from the axis of elongated retractor instrument 110 (FIG. 3A), and is additionally curved radially (FIG. 3B). As shown in FIGS. 3A and 3B, ipsilateral retraction blade 122 is shorter and has a greater cross-sectional (radial) curvature than contralateral retraction blade 120. In addition, ipsilateral blade 122 has a greater longitudinal curvature than contralateral blade 120.

A pair of angled extension members 117, 119 can extend from handle portion 112 to improve the access angle provided by the retractor instrument. Conventional retraction instruments are not well suited for approaches that are not directly lateral to an implantation site. The increased distance from the handle to the blades and the change in angle provided by extension members 117, 119 improve access to the implantation sites for the methods described herein.

In particular, extension members 117, 119 can extend from handle portion 112 such that they are substantially parallel to one another and form an angle of between about 45 and 80 degrees from a plane formed by a surface of handle portion 112 to which extension members abut and from which extension members extend. As shown in FIG. 22, extension member 119 is preferably shorter than extension member 117. If desired, a central angled extension member 121 can be provided between extension members 117, 119 to receive another blade member. Arms 116, 118 (FIG. 3A) are coupled to extension members 117, 119, respectively.

Arms 116, 118 and their respective retraction blades 120, 122 can be moved toward and away from one another by the movement of handles 124, 126, generally as shown in U.S. Pat. No. 7,207,949. Preferably, handles 124, 126 are coupled to a gear mechanism that converts the movement of the handles toward each other into linear movement of retraction arms 116, 118 away from one another to widen the distance between those arms without rotating them. The distance between handles 124, 126 can be adjusted and fixed by rotation of knobs 134, 136.

The retraction instrument 110 is placed in cannulated fashion over the dilators with the shorter ipsilateral arm/retraction blade on the ipsilateral side of the operative corridor. Retraction instrument 110 is slightly opened by moving handles 124, 126 toward one another so that opposing retraction arms 116, 118 move farther apart without rotation of the retraction arms. A standard xenon light source is carried by the instrument, and it is used for visualization of the anatomy at the distal tip of the instrument to position the retractor blades between the bifurcation of the right and left common iliac arteries and veins. The foot of ipsilateral blade 122 is placed beneath the ipsilateral vasculature (the right side for the approach illustrated in FIG. 3A) and the foot of contralateral blade 120 is placed under the contralateral vasculature (the left side for the approach illustrated in FIG. 3A). Handles 124, 126 are then moved closer together and fixed in position to move retraction arms 116, 118 away from one another and create surgical exposure of the anterior spine by moving ipsilateral vessels 66, 67 posteriorly and laterally with ipsilateral blade 122, and by moving contralateral vessels 68, 69 anteriorly and laterally with contralateral blade 120. Handles 124, 126 can be moved and fixed in different positions by rotation of knobs 134, 136.

FIGS. 5A and 5B illustrate retraction of the iliac vasculature to expose the L5-S1 intervertebral space; FIG. 5B also shows the trajectory along which retraction instrument 110 may be advanced. FIG. 5A shows the iliac vasculature running along the anterior spine near the front of the L5-S1 intervertebral space 70. FIG. 5B illustrates the iliac vessels retracted away from the anterior face of the spine by the retractor instrument 110 (not shown). A trajectory along which retractor instrument 110 may be introduced is shown by arrow 128 in FIG. 5B. The illustrated trajectory is from anterolateral incision 92 through the region of notch 36 between anterior superior iliac spine 32 and anterior inferior iliac spine 34. This trajectory contrasts with trajectory 130 (dotted line in FIG. 5B) taken by prior minimally invasive direct lateral surgeries for the L4-L5 disc space from the axillary line.

According to one aspect of the invention, once satisfactory ipsilateral vascular retraction is achieved, a shim 132 (FIGS. 3A and 4A, 4B, 4C) is inserted along the ipsilateral blade and advanced to position shim 132 within the anterolateral region of the L5-S1 disc space. Referring to FIGS. 22 and 23A-23C, blades 120, 122 can each be provided with a slot 133 for receiving a shim 132. FIG. 22 illustrates blade 122 with a shim 132 in slot 133, while blade 120 of FIG. 22 is shown without a shim or other structure positioned within its respective slot 133.

Shim 132 is an elongated plate with a substantially planar proximal portion 130*a* and a curved distal portion 130*b*. The curved distal portion 130*b* also tapers to a pointed distal tip 131 that is designed for introduction into an intervertebral space. The substantially planar proximal portion of shim 132 has a height h greater than its thickness t to minimize obstruction of access to the disc space when the shim is in place, and the height of the shim narrows anteriorly to pointed distal tip 131. Shim 132 further has a reversed curvature, in that its distal portion 130*b* is curved away from ipsilateral retraction blade 122 and toward contralateral retraction blade 120.

The curvature of the distal portion of shim 132 is relatively slight, being only 5-15 degrees out of the plane of the planar proximal portion 130*a* of shim 130. Alternatively, as shown in FIGS. 18A, 18B, and 18C, shim 132 can be substantially straight along its entire length. Shim 132 is attached to ipsilateral blade 120 to help lock retractor instrument 110 in position until removal of the instrument is desired, and distracts the adjacent vertebral bodies (such as L5 and S1) to restore disc height. Shim 132 can be coupled to ipsilateral blade 120 and/or contralateral blade 122 in a variety of manners. In a preferred embodiment, shim 132 comprises a projecting portion 135 that projects outward from a surface of shim 132. Projecting portion 135 can be a spring-loaded member that is biased outward from the surface of shim 132. In use, shim 132 can be positioned in a slot 133 and secured thereto to the respective blade (e.g., blade 122 in FIG. 23C).

Figure 21:
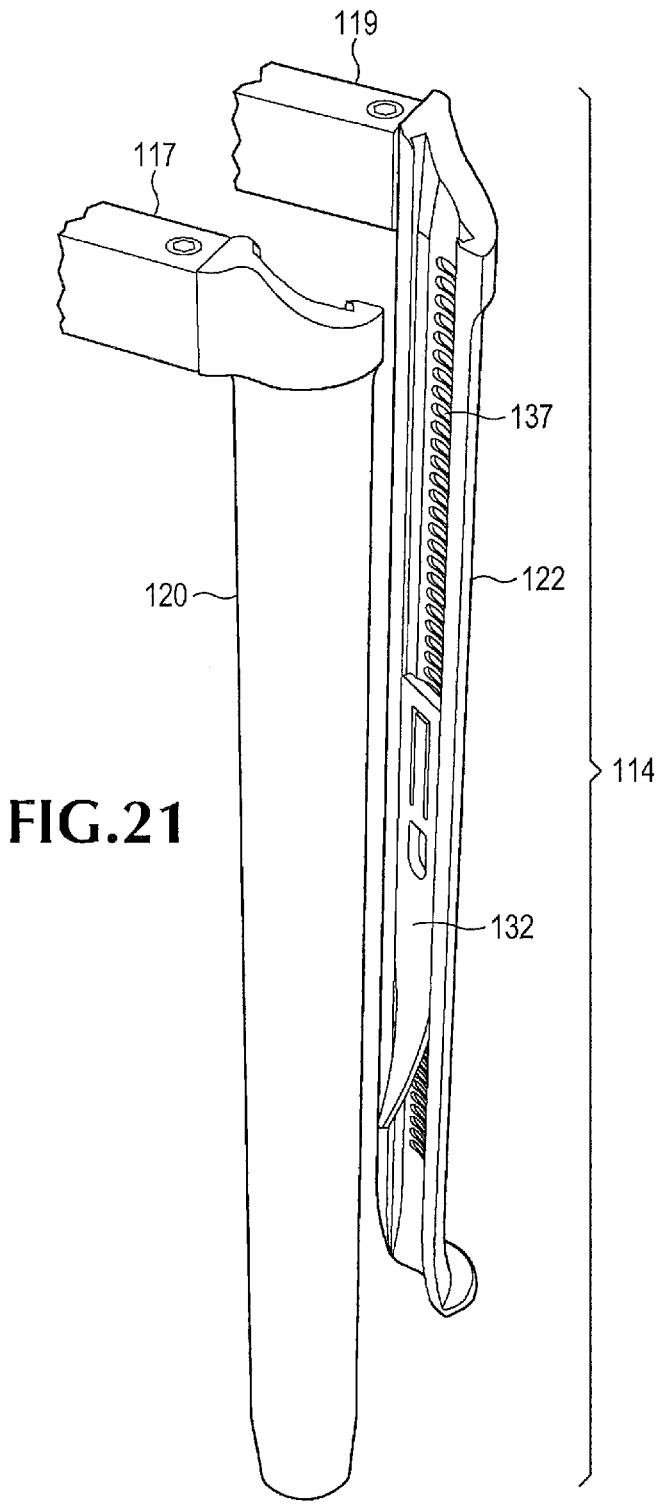
FIG. 21 is a perspective view of a portion of a retraction instrument with a pair of blades provided at a distal end.
Figures 23A, 23B:
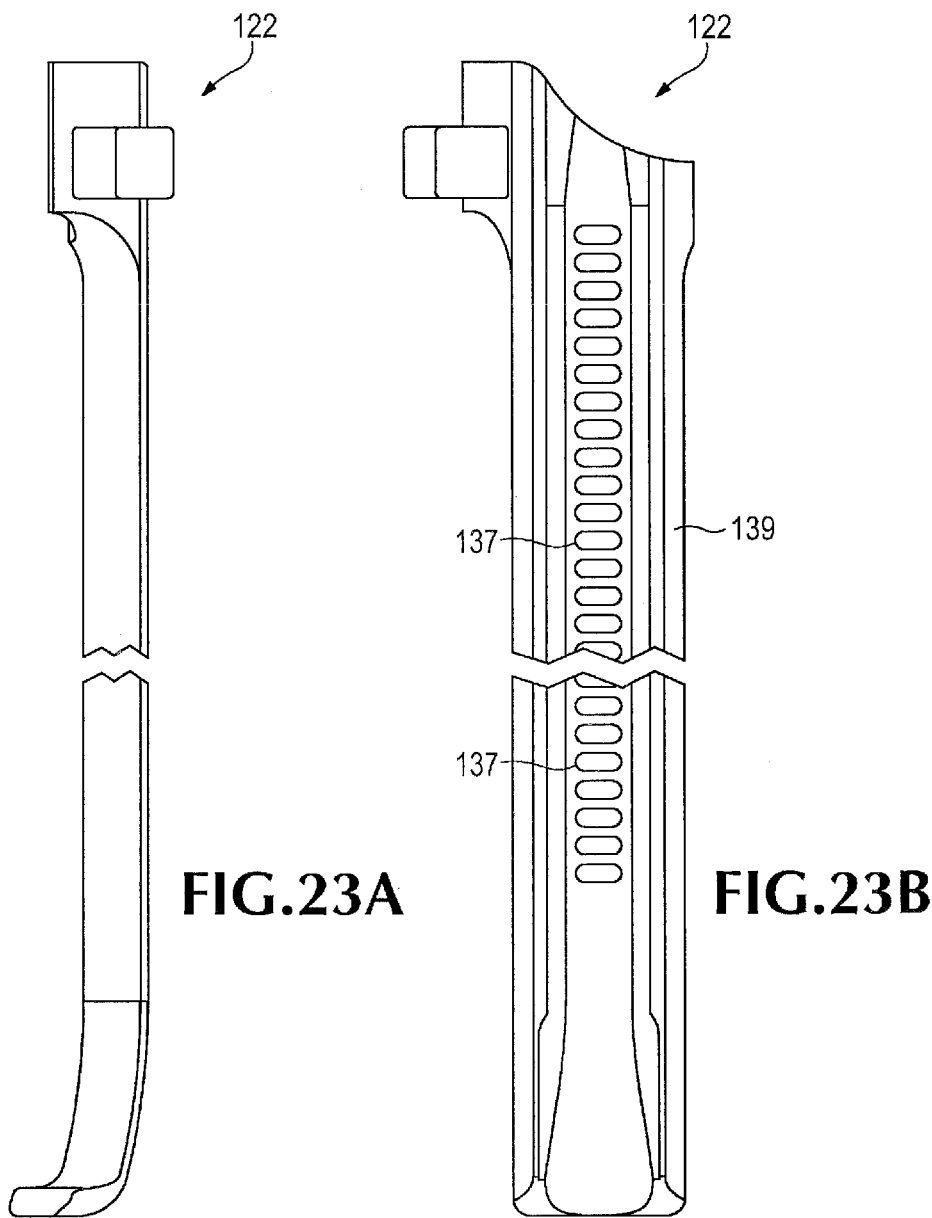
FIG. 23A is a perspective view of a blade for use with a retraction instrument.
FIG. 23B is a rear view of the blade of FIG. 23A.
Figure 23C:
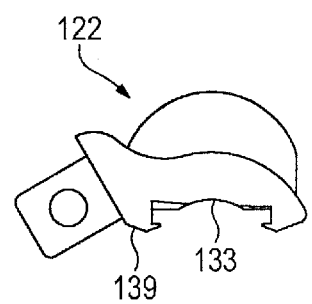
FIG. 23C is a top view of the blade of FIG. 23A.

As shown in FIGS. 21 and 23B, a plurality of spaced detents or openings 137 can extend along the length of a rear side 139 of blade 122 to receive projecting portion 135 and secure shim 132 to blade 122. When projecting portion 135 is in a locked position (i.e., with projecting portion 135 extending at least partially through a detent 137), shim 132 is restricted from moving relative to blade 122. To adjust the position of shim 132 relative to blade 122, projecting portion 135 can be pushed inward towards the surface of shim 132, moving projecting portion 135 out of detent 137 and releasing shim 132 from blade 122. Once projecting portion 135 is released from detent 137, shim 132 can be moved into another position along blade 122 by pushing or otherwise directing shim 132 downward along the length of blade 122. This process can be repeated until shim 132 is secured to blade 122 in a desired position.

Shim 132 also rigidly couples ipsilateral retractor blade 122 in fixed relation relative to the vertebral bodies, and helps ensure that surgical instruments employed within the operative corridor are not advanced outside the operative corridor, thereby avoiding inadvertent contact with the exiting nerve roots and vasculature during the surgery. Once the operative corridor is established, any of a variety of surgical instruments, devices, or implants may be passed through and/or manipulated within the operative corridor depending upon the given surgical procedure.

Superior and inferior soft tissue retractors (not shown) may also be placed as needed for retraction for any creeping retroperitoneal contents to allow creation of a box-type approach to the L5-S1 disc space. Discectomy is than carried out in a conventional fashion to evacuate as much of the disc and interspace contents as possible. The handle portion 112 may be coupled to any number of mechanisms for rigidly registering it in fixed relation to the operative site, such as through the use of an articulating arm mounted to the operating table 22.

Introducer Instrument

Once the discectomy has been completed, trial implants are introduced into the L5-S1 disc space 70 to select an appropriate size final implant, and a final implant is then introduced into the disc space.

FIGS. 6-9 illustrate an introducer instrument 140 for introducing implants into the disc space. Instrument 140 includes a rigid sheath 142 (FIGS. 6-7) that is sufficiently long to reach the L5-S1 disc space 70. A longitudinal axis 144 of sheath 142 is illustrated by a dashed line. Instrument 140 is provided with a proximal handle 146 that is coupled to a rotatable shaft 147 (FIG. 8) inside a ridged collar 148 (FIG. 7) so that shaft 147 can be rotated within sheath 142 by rotating handle 146 as collar 148 is grasped by the surgeon's hand to maintain collar 148 stationary. As shown in FIG. 7, an externally threaded rod 150 projects from a cylindrical distal tip 152 of sheath 142 along longitudinal axis 144 on sheath 142. A pair of small coupling pins 154, 156, which are smaller than threaded rod 150, project from distal tip 152 on either side of rod 150 in a fixed spaced alignment generally along a common plane that bisects shaft 142 along its axis 144. Coupling pins 154, 156 are substantially shorter and of much smaller diameter than the threaded rod 150. For example, coupling pins are less than 25% or even 10% of the diameter and length of threaded rod 150 projecting from the tip 152 of instrument 140.

As shown best in FIG. 8, threaded rod 150 is connected to rotatable shaft 147 by a reduced diameter step-down extension 158 that projects out of distal tip 152 of sheath 142 to provide a gap between threaded rod 150 and the face 160 of distal tip 152. Distal tip 152 (and pins 154, 156 that it carries) can be selectively advanced toward and retracted from implant 172 in a pathway generally parallel to longitudinal axis 144 by rotating handle 146. As handle 146 rotates counterclockwise, it drives shaft 147 to turn threaded rod 150 and loosen the connection between rod 150 and a threaded opening in the implant. Since pins 154, 156 have a much shorter axial length than threaded rod 150, only slight loosening of the threaded rod is required to disengage pins 154, 156 from the implant. Once pins 154, 156 are disengaged from the implant, they can be repositioned in another set of openings on the implant to change the angle between instrument 140 and the implant. Handle 146 is then rotated clockwise to tighten the pins in their new openings to fix the new angular relationship between instrument 140 and the implant.

Threaded rod 150 and coupling pins 154, 156 form an example of a docking element of introducer instrument 140. The docking element selectively docks with an interface element 170 of an implant 172, as shown in FIG. 9. The docking element docks at a plurality of positions with interface element 170 to selectively alter an angle between implant 172 and introducer instrument 140. Implant 172 has a pivot axis 174 around which implant 172 may be pivoted relative to longitudinal axis 144 of instrument 140.

Figure 10A:
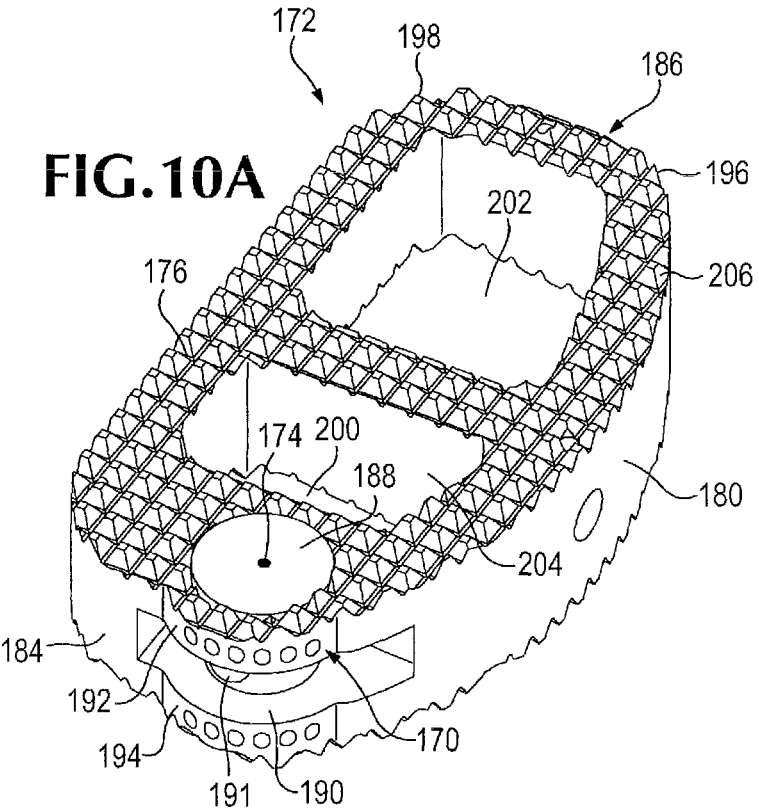
FIG. 10A is a perspective view of a first embodiment of the implant, showing the implant interface surface in which pairs of pin receiving holes are arranged at different angles around the interface surface to hold the implant at variable fixed angles relative to the longitudinal axis of the introducer instrument.
Figure 10B:
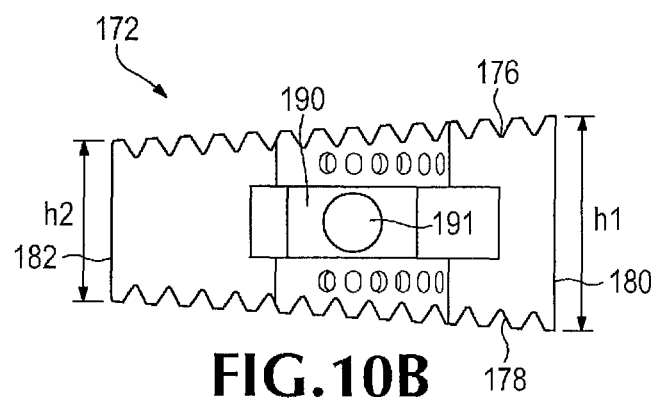
FIG. 10B is an end view of the implant of FIG. 10A, illustrating a tapered height of the implant.

An example of an implant 172 is shown in greater detail in FIGS. 10A and 10B, where implant 172 has a top bearing face 176, a bottom bearing face 178, a front face 180, a rear face 182, an ipsilateral face 184 and a contralateral face 186.

A rotation pin 188 extends between top and bottom faces 176, 178 and rotates relative to implant 172; pivot axis 174 of implant 172 extends along the axis of rotation pin 188. Interface element 170 (FIGS. 9 and 10A) has a recessed slot 190 between top and bottom faces 176, 178 that provides access to the side of rotation pin 188 in which an internally threaded opening 191 is provided which has threads that are complementary to the external threads of rod 150 of introducer instrument 140. An upper arcuate lip 192 and lower arcuate lip 194 form slot 190 cooperatively therebetween. Lips 192, 194 are spaced from and generally parallel to the outer walls of rotation pin 188. Lips 192, 194 of interface element 170 each have a series of spaced docking holes that form paired upper and lower sets of spaced holes arranged on the curved surfaces of the lips. These docking holes extend partially circumferentially around pivot axis 174, and selected pairs of spaced docking holes are positioned to mate with the docking element of introducer instrument 140. This docking is illustrated in greater detail in FIG. 9 wherein face 160 of distal tip 152 is curved to fit in register with the curved faces of lips 192, 194 with pin 154 in an upper member of a docking pair of holes on upper lip 192 and pin 156 (not shown in FIG. 9) in a corresponding aligned lower member of the docking pair of holes on lower lip 194. Interface element 170 therefore includes spaced docking holes that extend partially circumferentially around pivot axis 174 so that selected pairs of docking holes are positioned to mate with the docking element of introducer instrument 140.

In use, introducer instrument 140 is secured to an implant 172 by threading rod 150 into opening 191 of rotation pin 188 by rotating handle 146 to turn shaft 147 within sheath 142. Handle 146 is rotated until implant 172 is tightly secured to distal tip 152 and pins 154, 156 are aligned with and inserted within a pair of the upper and lower aligned docking holes. The angular relationship between instrument 140 and implant 172 can be altered by slightly unscrewing threaded rod 150 from threaded opening 191. This action moves face 160 of distal tip 152 sufficiently out of engagement with interface element 170 to disengage pins 154, 156 from a first set of docking holes without completely disconnecting instrument 140 from implant 172. The implant 172 and instrument 140 can then pivot relative to one another until sheath 142 is again advanced to engage coupling pins 152, 154 with a new pair of docking holes by rotating handle 146 to once again securely engage instrument 140 to implant 172, so that the implant is fixed at a new angular relationship with the instrument.

Although a particular embodiment of the device is illustrated in which the angular relationship between instrument 140 and implant 172 can be selectively altered, many other means for varying this angular relationship to pivot the implant are contemplated. For example, rotation of handle 146 can actuate a gear that pivots implant 172, or handle rotation can actuate a cam that selectively moves pins 154, 156 to selectively engage and disengage them from interface element 170. Alternatively the tip of instrument 140 can fit into a slot within implant 172 to pivot the implant as instrument 140 is moved from the contralateral to the ipsilateral arm of the retractor instrument. In other embodiments, a universal joint is provided between the instrument 140 and implant 172 to selectively pivot the implant relative to the instrument. Different numbers and arrangements of the pins can also be provided. Electronic devices can also be used that rotate the implant in the plane of the disc space while maintaining the instrument within the operative pathway defined between the retraction blades of instrument 140.

The Implant

Additional features of implant 172 are shown in detail in FIGS. 10 and 11 to illustrate details that make the implant particularly suitable for insertion and progressive pivoting of the implant within the L5-S1 disc space, as described in greater detail below. The implant tapers in height from the height h1 of front face 180 to height h2 of rear face 182, and is elongated in a direction transverse to the direction of tapering height. Hence front face 180 and rear face 182 are longer than ipsilateral and contralateral faces 184, 186. The implant material is made of a generally compressible or elastomeric material. Front face 180 is generally convex, ipsilateral face 184 includes interface element 170, rear face 176 is generally flat, and contralateral face 186 is rounded at its front and rear edges to minimize impact damage to spinal structures as the implant is introduced into the disc space and pivoted into position. Implant 172 is also partially hollow and may have ipsilateral and contralateral windows 200, 202 extending between top and bottom faces 176, 178. The windows are formed by an internal divider wall 204 that extends from the front to rear of implant 172 and substantially bisects the implant into ipsilateral and contralateral halves. However, ipsilateral window 200 is smaller than contralateral window 202 because a portion of the ipsilateral half of implant 172 is occupied by rotation pin 188 and the structure that supports it. The windows 200, 202 provide communication between the open bottom and top faces of the implant to promote ingrowth of tissue within and through implant 172.

Top and bottom faces 176, 178 are provided with protuberances 206 that also help promote bone growth into implant 172. The protuberances may take a variety of shapes, but the illustrated frustopyramidal protuberances 206 are believed to be particularly suitable for this purpose.

In addition to the implant, trial spacers are also provided to help assess the size of the disc space once the disc space contents have been evacuated but before the final implant is advanced into the disc space.

Figure 11A:
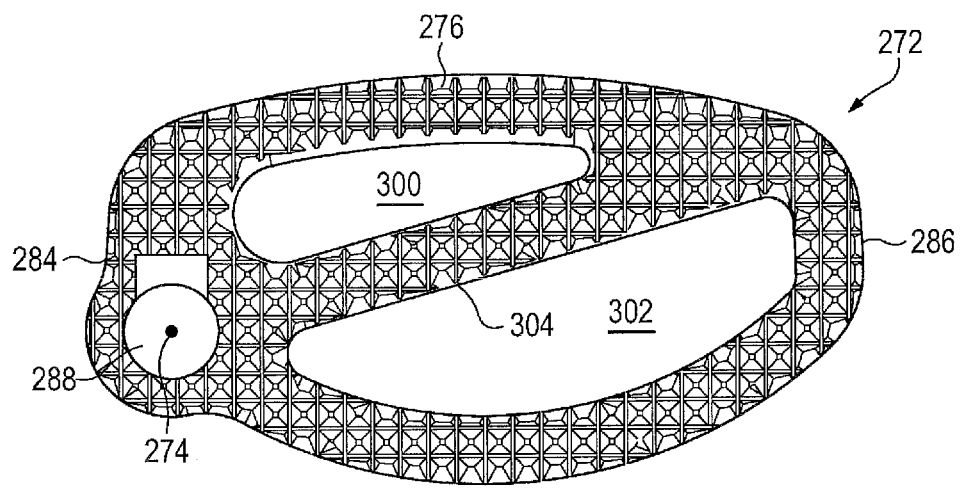
FIG. 11A is a top view of an embodiment of an implant.
Figure 11B:
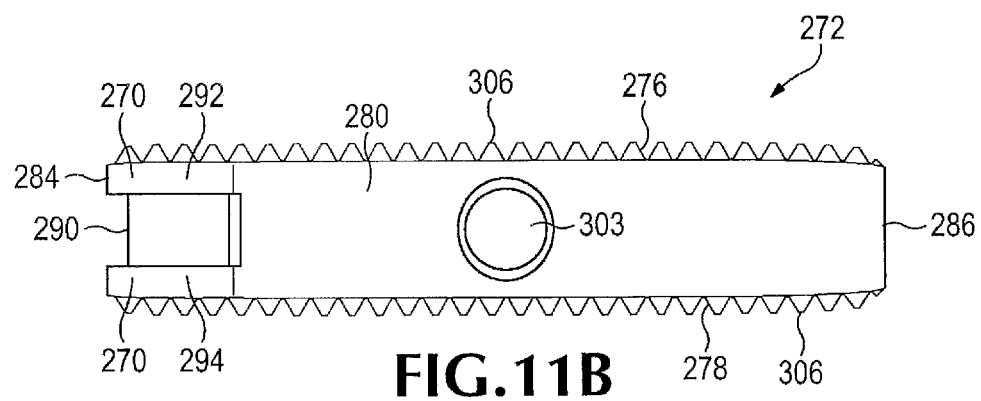
FIG. 11B is a side view of an embodiment of the implant of FIG. 11A.
Figure 11C:
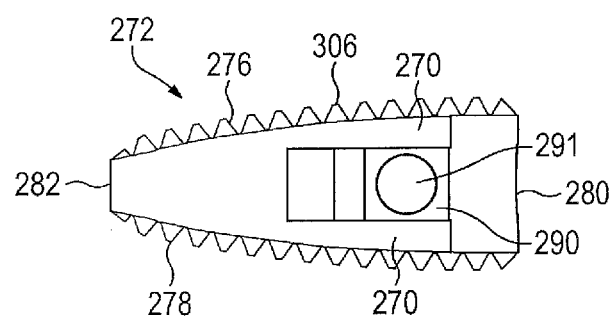
FIG. 11C is an end view of an embodiment of the implant of FIG. 11A.

FIGS. 11A, 11B, and 11C illustrate another embodiment of an implant 272. To facilitate comparison to implant 172, FIGS. 11A-C use reference numbers with the same two final digits for elements that are generally similar to elements identified in FIGS. 10A and 10B. Thus, implant 272 has a top bearing face 276, a bottom bearing face 278, a front face 280, a rear face 282, an ipsilateral face 284 and a contralateral face 286. A rotation pin 288 extends between top and bottom faces 276, 278 and rotates relative to implant 272. Pivot axis 274 of implant 272 extends along the axis of rotation pin 288.

An interface element 270 (FIGS. 11B and 11C) has a recessed slot 290 between top and bottom faces 276, 278 that provides access to the side of rotation pin 288 in which an internally threaded opening 291 is provided which has threads that are complementary to the external threads of rod 150 of introducer instrument 140. An upper arcuate lip 292 and lower arcuate lip 294 form slot 290 cooperatively therebetween. For clarity, FIG. 11B is shown without pin 288 fitted or received in implant 272.

Lips 292, 294 of interface element 270 can have a series of spaced docking holes such as that shown in FIGS. 10A and 10B. Alternatively, as shown in FIGS. 11B and 11C, lips 292, 294 can be formed without such docking holes. Instead, the introducer instrument can be shaped to contact a portion of the upper and/or lower curved faces of lips 292, 294, thereby forming a frictional fit between the convex face of implant 272 and a concave face 160 of the introducer instrument 140. Thus, in use, introducer instrument 140 can be secured to implant 272 by threading rod 150 into opening 291 of rotation pin 288 by rotating handle 146 to turn shaft 147 within sheath 142. When handle 146 is rotated a sufficient amount, implant 272 will be tightly secured to face 160 of distal tip 152. The angular relationship between instrument 140 and implant 272 can be altered by slightly unscrewing threaded rod 150 from threaded opening 291. This action moves face 160 of distal tip 152 sufficiently out of engagement of the frictional fit with interface element 270 (or other contacting portion of a surface of implant 272). Implant 272 and instrument 140 can then pivot relative to one another until sheath 142 is again advanced to engage the instrument 140 and implant 272 in a frictional fit that is tight enough to restrict relative movement of the instrument 140 and implant 272.

As shown in FIGS. 11B and 11C, implant 272 can be constructed so that it is substantially the same thickness (height) along its length (FIG. 11B), while at the same time varying in thickness (height) along its width (FIG. 11C). In particular, as shown in FIG. 11C, the thickness (height) of implant 272 can vary from a first larger height to a second smaller height to facilitate the implantation of the device in the patient.

Like implant 172, implant 272 can be provided with protuberances 306 that help promote bone growth into implant 172. As noted above, such protuberances can take a variety of shapes. Also like implant 172, implant 272 can be at least partially hollow and can have one or more windows (e.g., windows 300, 302). Windows 300, 302 can provide the same benefits as windows 200, 202 in the previous embodiment, which is to provide communication between the open bottom and top faces of the implant to promote ingrowth of tissue within and through implant 272. Implant 272 can also have one or more openings 303 that extend through a side wall of the implant to further promote ingrowth of tissue and to facilitate access to internal areas of implant 272 (e.g., access to one or both of windows 300, 302) when implant 272 is implanted in the body.

Figure 20:
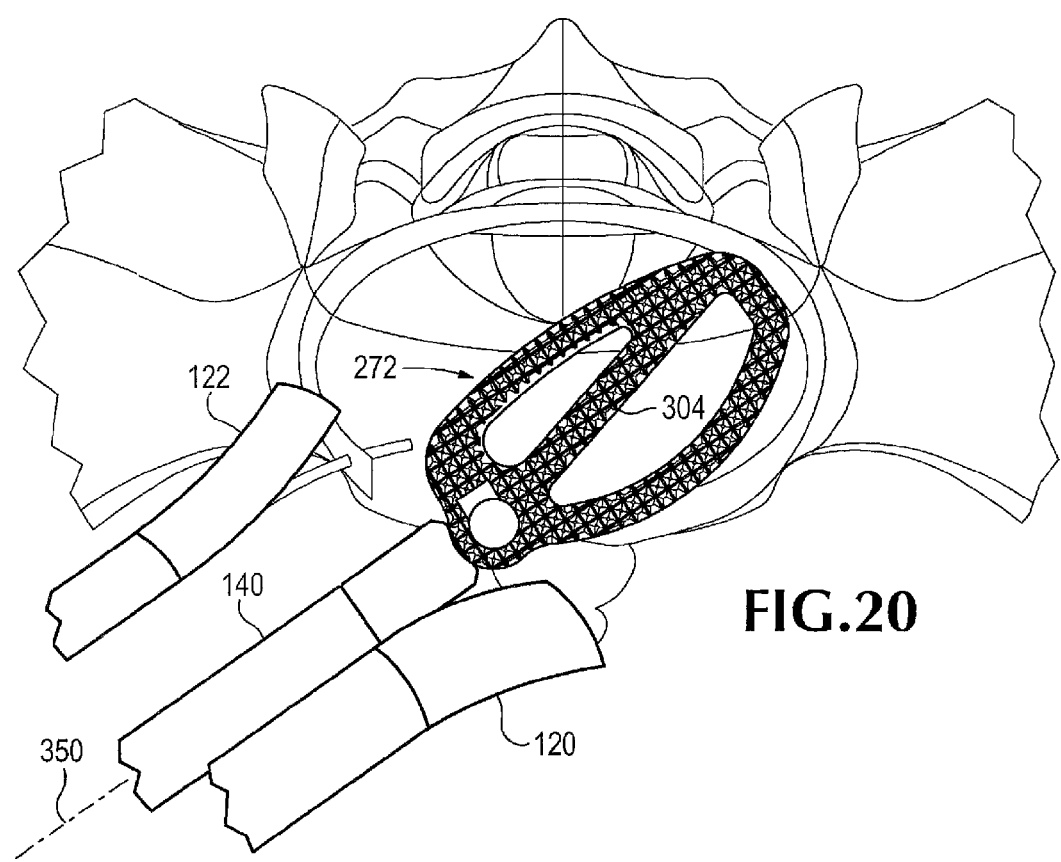
FIG. 20 is a top view of the L5-S1 disc space, illustrating orientation of the implant of FIG. 11A within a disc space.

Windows 300, 302 can extend between top and bottom faces 276, 278 as shown in FIG. 11A. The windows can be formed by an internal divider wall 304 that substantially bisect the implant into two halves. Unlike divider wall 204 shown in FIG. 10A, however, divider wall 304 preferably extends diagonally across implant 272 from an area adjacent or near the pin 288 to an area at or near contralateral face 286. By extending generally diagonally across implant 272 as shown in FIG. 11A, diagonal wall 304 can provide structural strength to the implant in the general direction of the force that will be applied to implant 272 during implantation. For example, as shown in FIG. 20, divider wall 304 is located substantially in-line with the instrument 140.

FIG. 12 illustrates another version of an implant 220. This implant is similar to that shown in FIGS. 10-11, except it is substantially rectangular in shape instead of polygonal, and it has a rotation pin 222 with a pivot axis 224 that extends between a front and rear face of implant 220. Rotation pin 222 includes an opening 226 (e.g., a threaded opening) for receiving a threaded distal end of introducer instrument 140. As described above with respect to implant 172, implant 220 can be secured to threading rod 150 by positioning rod 150 into opening 226 and rotating handle 146 to turn shaft 147 and tighten the distal end of the instrument (e.g., face 160) to a facing surface of implant 220.

Because rotation pin 222 is positioned horizontally (FIG. 12) rather than vertically (FIG. 10A), implant 220 is therefore suitable for pivoting up and down with respect to introducer instrument 140 instead of from side-to-side as with implant 172. It may also have varied dimensions medial to lateral as described for implant 172, although other embodiments do not taper and are of uniform height. The embodiment of the implant shown in FIG. 12 is generally used in surgeries superior to the L5-S1 space, for example in the L4-L5 space or the L3-L4 space. By providing an implant that can pivot vertically, such as implant 220, the implantation site can be more easily accessed from an incision point superior or inferior to the implantation site. For example, in use, the implant can be delivered to the implantation site from a location superior to iliac crest 30 and pivoted vertically into the desired position at the implantation site.

Figure 19A:
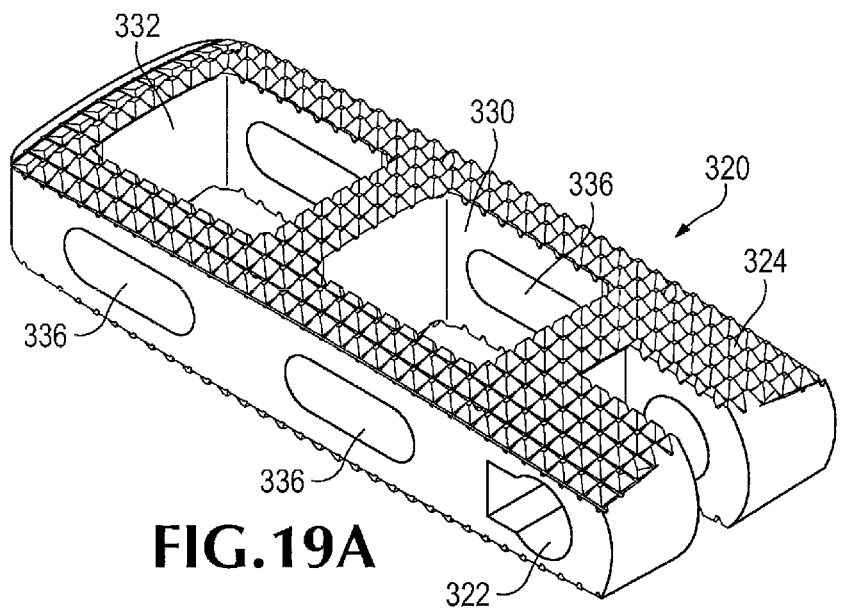
FIG. 19A is a perspective view of an embodiment of an implant.
Figure 19B:
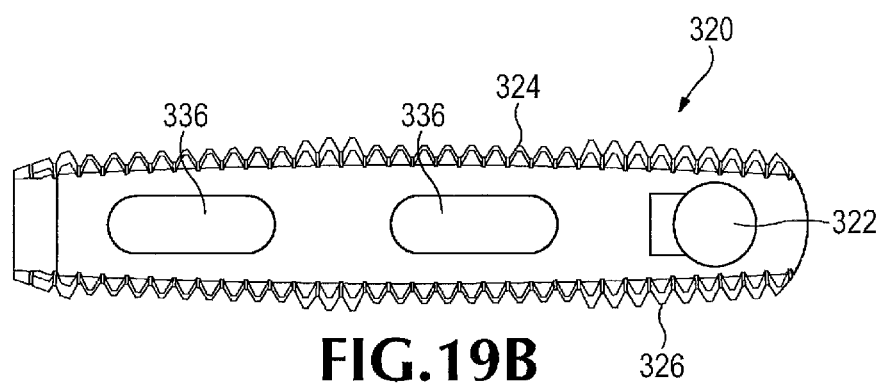
FIG. 19B is a side view of an embodiment of the implant of FIG. 19A.
Figure 19C:
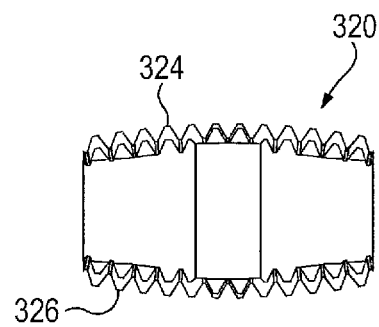
FIG. 19C is an end view of an embodiment of the implant of FIG. 19A.

As with the other implants described herein, implant 220 can be provided with one or more windows 228, 230 and a plurality of protrusions 232 to promote the ingrowth of tissue. Implant 220 can also be provided with a plurality of docking holes 234 to help lock or secure implant 220 to a distal end of instrument 140. Alternatively, implant 220 can be secured to the instrument 140 via a frictional fit or other similar mechanism. FIGS. 19A, 19B, and 19C illustrate another embodiment of an implant that can pivot up and down (e.g., vertically), in a manner similar to that shown in FIG. 12. Implant 320 is configured to receive a rotation pin (not shown) in a recess 322 between a top surface 324 and a bottom surface 326 of implant 320. As described in other embodiments, implant 320 can include a plurality of windows 330, 332 separated by a divider wall 334. In addition, openings 336 can be formed in the side of the implant as shown in FIGS. 19A and 19B.

Introducing the Trial Spacer and Disc Implant

Once the operative corridor has been established by retraction instrument 110 and the operative field has been exposed, a trial spacer 210 is attached to introducer instrument 140 and advanced into the L5-S1 disc space as shown in FIG. 13. The trial spacer is generally similar to implant 174, except it does not have the protuberances projecting from its top and bottom faces. For the initial introduction of trial spacer 210, the spacer is directly laterally attached to instrument 110. The direct lateral attachment is shown in FIG. 13, wherein the longitudinal axis of sheath 142 is generally parallel to flat rear face 182 of implant 210. Because of the anterolateral operative pathway to the disc space, trial implant 210 moves along a generally oblique or diagonal pathway into the disc space. The "oblique" pathway is one that travels diagonally within the body, for example in an oblique anatomic plane. The oblique pathway may be a diagonal pathway, for example between 15 and 45 or 60 degrees to a coronal plane of the body. In FIG. 13, the oblique pathway is shown at an angle α of about 30 degrees to coronal plane 212 (FIG. 13). The oblique pathway may be either in a transverse plane of the body, or above or below a transverse plane (for example between 15 and 45 or 60 degrees to a transverse plane of the body). However, in a particular disclosed embodiment of the method, fluoroscopy is used to detect the level of the target disc space (such as L5-S1) so that the instrument, spacer and implant can be introduced diagonally in the body, but generally in the plane of the L5-S1 disc space.

As trial spacer 210 enters the illustrated L5-S1 disc space (FIGS. 13 and 14A), contralateral face 186 impacts the posterior contralateral aspect of the disc space. The rounded edges of contralateral face 186 help avoid damage to the structures which the contralateral face 186 of the trial spacer encounters. The trial spacer is then progressively reoriented from its diagonal orientation in the disc space (FIG. 14A) to a generally medial-lateral orientation (FIG. 14C) by successively retracting sheath 142, pivoting the trial spacer on rotation pin 188 by forcing contralateral face of trial spacer 210 against the postero lateral apophyseal ring and moving introducer instrument 140 toward ipsilateral retractor arm 118, and repositioning coupling pins in a new set of docking holes that maintain the trial spacer in an intermediate position shown in FIG. 14B. Sheath 142 is then retracted again, and the trial spacer pivoted on rotation pin 188 to the generally medial-lateral orientation (FIG. 14C). As the trial spacer 210 moves from its initial diagonal to final medial-lateral orientation (with its flat rear face generally parallel to a coronal plane of the body), sheath 142 moves from a first position abutting contralateral retractor blade 120 (FIG. 14A) to a second position abutting ipsilateral blade 122 (FIG. 14C).

Figure 16B:
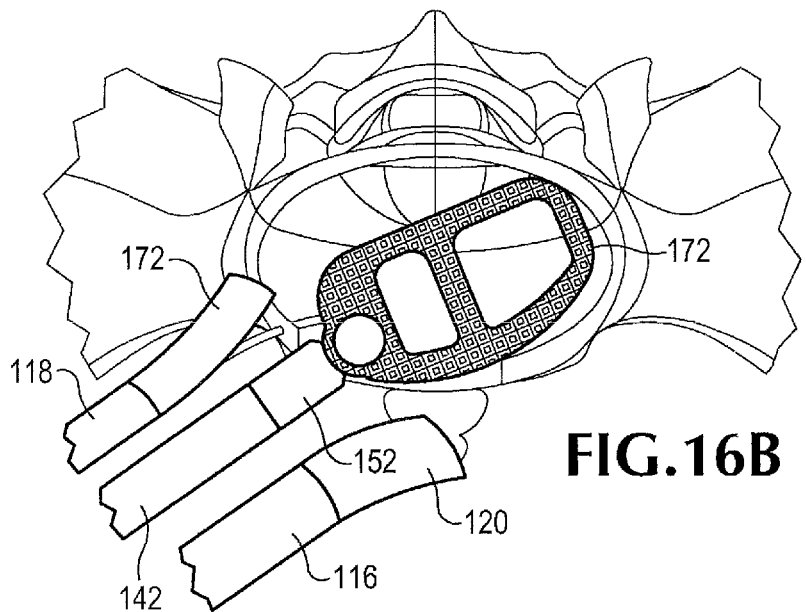
Figure 16C:
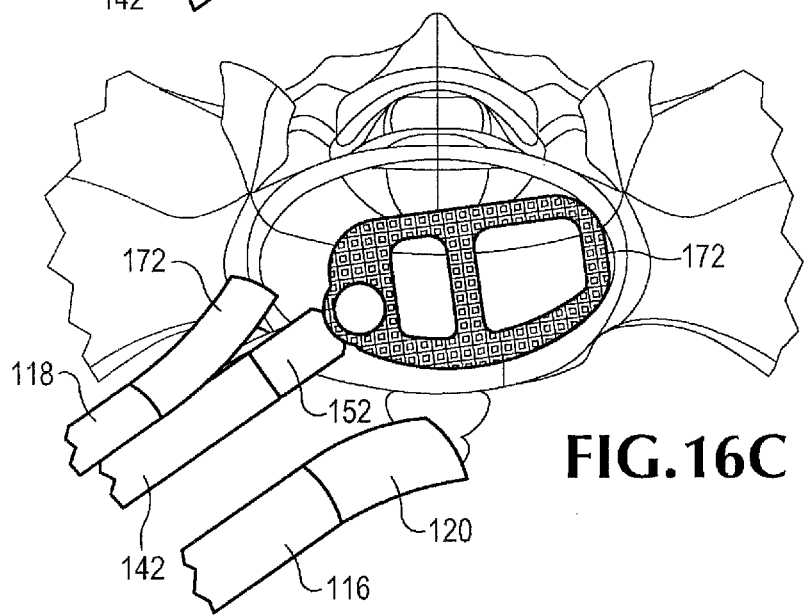

Trial spacers of different sizes may be introduced into the disc space and pivoted from the diagonal to the medial-lateral orientation until a trial spacer of the appropriate size and height is found. Introducer instrument 140 is detached from trial spacer 210 by rotating handle to unscrew threaded 150 from the internally threaded opening of trial spacer 210 to secure different trial spacers until the correct one is found. The trial spacer is then withdrawn from the disc space and detached from introducer instrument 140, and the final implant 172 is directly laterally attached to distal tip 152 of introducer instrument 140 (as illustrated in FIG. 15) by rotating handle 146 to screw the threaded rod at the tip of instrument 140 into the internally threaded hole on the implant. With the implant 172 directly laterally attached to instrument 141, the elongated implant 172 can be introduced through a relatively narrow operative pathway between the arms of retractor instrument 110. FIG. 16A illustrates the diagonal introduction of implant 172 into the disc space along the same pathway already described for trial spacer 210. The implant enters the disc space with its flat rear face 182 at an angle of about 15-45 degrees (for example 30 degrees) to a coronal plane of the body. The implant is then progressively reoriented by retracting sheath 142, pivoting implant 172 within the disc space, and advancing sheath 142 to reengage coupling pins 154, 156 within a new set of docking holes to hold implant 172 in the intermediate orientation shown in FIG. 16B wherein the implant is at an angle of about 15 degrees to a coronal plane of the body. Implant 172 can then be further reoriented in this fashion until sheath 142 contacts ipsilateral arm 118 of retractor instrument 110 (FIG. 16C). Once implant 172 can not be reoriented any further using the instrument, handle 146 is rotated to completely disengage introducer instrument 140 from implant 172. Instrument 140 is then withdrawn from retractor instrument 110.

Additional positioning of implant 172 can be achieved by pushing it with the tip of instrument 140, or with other elongated instruments introduced through retractor instrument 110. Retractor instrument 110 can then be removed from the body by moving arms 116, 118 toward one another to reduce the width of instrument 110 then withdrawing it from the body. Normal closure of the surgical incisions on the body surface is then carried out.

Figure 17:
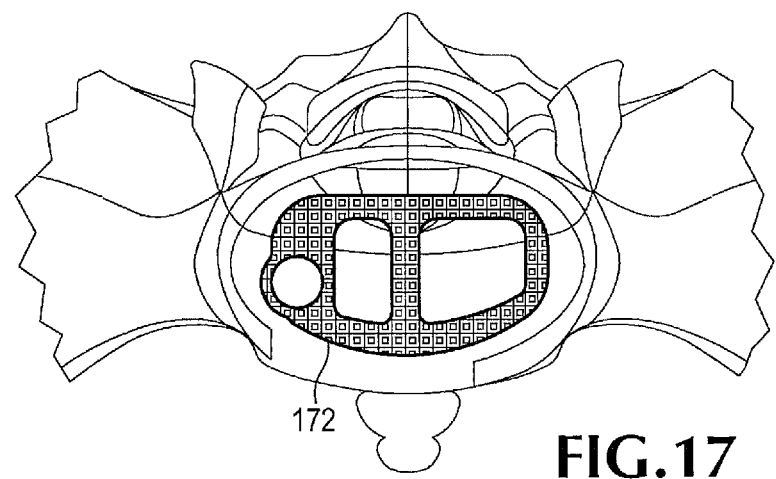
FIG. 17 is an enlarged top view of the L5-S1 disc space illustrating the implant in position within the disc space.

FIG. 20 illustrates implant 272 secured to instrument 140 and being delivered to an implantation site. The method of delivering implant 272 is substantially the same as the method of delivering implant 172, which is described above and shown in FIGS. 15-17.

Implant 272 is desirably secured to the distal end of instrument 140 so that divider wall 304 is generally in-line with axis 350 of instrument 140. In this manner, implant 272 can exhibit increased strength to ensure that it can withstand the impaction force, which is generally applied along the axis 350 to deliver implant 272 to the desired location in the body.

The implants described herein can be coated with and/or impregnated with various elements to promote bone in-growth. In a preferred embodiment, stem cells can be delivered along with the implant (either delivered into openings in the implant or coated thereon) to improve and facilitate bone in-growth. In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A method of positioning a spinal implant into an intervertebral space of a subject, comprising:
    establishing an anterolateral operative corridor in a subject, while the subject is positioned on his/her side, wherein the anterolateral operative corridor extends from the subject's skin to a location proximate an anterolateral portion of an intervertebral space between the L5 and S1 vertebrae, wherein establishing the anterolateral operative corridor comprises:
        inserting a retractor into the subject while the subject is positioned on his/her side, wherein a distal portion of the retractor comprises:
            a first retraction blade;
            a second retraction blade, wherein the first and second retraction blades are inserted between iliac vessels of the subject proximate the anterolateral portion of the intervertebral space; and
        at least partially expanding the retractor to establish the anterolateral operative corridor, wherein iliac vessels are separated apart such that one iliac vessel at least partially moves in an anterior direction towards a front of the subject and one iliac vessel at least partially moves in a posterior direction towards a back of the subject;
    advancing the spinal implant at least partially into the intervertebral space between the L5 and S1 vertebrae via the anterolateral operative corridor, wherein the spinal implant is advanced into the intervertebral space at an oblique angle to the intervertebral space; and
    rotating the spinal implant at least partially within the intervertebral space.

2. The method of claim 1, wherein the anterolateral operative corridor extends in an anterolateral direction to the anterolateral portion of the intervertebral space such that the anterolateral operative corridor provides access to the intervertebral space via the anterolateral direction.

3. The method of claim 2, wherein advancing the spinal implant to the intervertebral space comprises inserting the spinal implant at least partially into the intervertebral space in a first orientation such that the longitudinal axis of the implant is oriented substantially parallel to the anterolateral direction.

4. The method of claim 2, further comprising inserting one or more dilators in the anterolateral direction.

5. The method of claim 1, wherein the anterolateral operative corridor is oblique to the coronal plane of the subject and the median plane of the subject.

6. The method of claim 1, wherein the anterolateral operative corridor approximately bisects an angle formed between the coronal plane of the subject and the median plane of the subject.

7. The method of claim 1, wherein the anterolateral operative corridor comprises a pathway that extends substantially between a surface incision in the subject's skin and the intervertebral space.

8. The method of claim 1, wherein the retractor comprises a longitudinal axis, wherein the longitudinal axis of the retractor is positioned along an anterolateral path extending between an incision in the subject's skin and an implant insertion location proximate an anterolateral portion of the intervertebral space.

9. The method of claim 1, wherein advancing the spinal implant to the intervertebral space comprises orienting a longitudinal axis of the implant to be substantially parallel to the direction of advancement.

10. The method of claim 1, wherein rotating the spinal implant comprises rotating the spinal implant to an orientation such that the longitudinal axis of the implant is oriented substantially parallel to the coronal plane of the subject.

11. The method of claim 1, wherein the implant is pivotably coupled to a distal end of an elongate introducer instrument, and wherein rotating the spinal implant comprises pivoting the implant relative to the distal end of the introducer instrument.

12. The method of claim 1, further comprising positioning a distal end of the first and the second retraction blades at an anterior face of a vertebra adjacent an anterior longitudinal ligament.

13. The method of claim 1, further comprising spreading the first and the second retraction blades to expose an area from about a 10 o'clock to a 2 o'clock position of the vertebra.

14. The method of claim 1, wherein the anterolateral operative corridor is at least partially obliquely positioned relative to an anterior face of the spinal disk between the L5 and S1 vertebrae.

15. The method of claim 1, wherein the spinal implant is rotated to position the spinal implant substantially medial-laterally within the intervertebral space.

16. The method of claim 1, wherein the first retraction blade is curved away from a longitudinal axis of the retractor.

17. The method of claim 1, wherein the second retraction blade is curved away from a longitudinal axis of the retractor.

18. The method of claim 1, further comprising a shim coupled, during use, to the first or the second retractor blade, wherein the shim comprises a curved distal portion, and wherein the curved distal portion is curved away from a longitudinal axis of the retractor blade when coupled to the first or the second retractor blade.

19. The method of claim 1, wherein the first or the second retraction blade comprises curved surfaces.

20. The method of claim 1, wherein the first and second retraction blades are inserted such that the iliac vessels are separated apart such that one iliac vessel at least partially moves in an anterior direction and one iliac vessel at least partially moves in a posterior direction.

21. The method of claim 1, wherein the iliac vessels are separated apart to create a space for advancing the spinal implant between the iliac vessels by moving one iliac vessel at least partially in an anterior direction and one iliac vessel at least partially in a posterior direction.

22. The method of claim 1, wherein the spinal implant is advanced into the vertebral space between the L5-S1 vertebrae by advancing between the iliac vessels, wherein the iliac vessels have been separated apart, to create a space for advancing the spinal implant, by moving one iliac vessel at least partially in an anterior direction and one iliac vessel at least partially in a posterior direction.

23. The method of claim 1, wherein the anterolateral operative corridor is substantially anterior to the psoas muscle.

24. The method of claim 1, wherein the iliac vessels are ipsilateral and contralateral iliac vessels;
using the first retraction blade of the retractor to move the ipsilateral iliac vessels posteriorly and laterally; and
using the second retraction blade of the retractor to move the contralateral iliac vessels anteriorly and laterally, wherein the ipsilateral iliac vessels and the contralateral iliac vessels are moved away from the anterolateral portion of the intervertebral space.

25. The method of claim 1, further comprising establishing the anterolateral operative corridor in the subject in a minimally invasive manner.

26. A method of positioning a spinal implant into an intervertebral space of a subject, comprising:
establishing an anterolateral operative corridor in a subject, while the subject is positioned on his/her side, wherein the anterolateral operative corridor extends from the subject's skin to a location proximate an anterolateral portion of an intervertebral space between the L5 and S1 vertebrae, wherein establishing the anterolateral operative corridor comprises:
inserting a retractor into the subject while the subject is positioned on his/her side such that a distal portion of the retractor is positioned between a right and a left iliac vessels;
at least partially expanding the retractor to establish the anterolateral operative corridor comprising:
using a first retraction blade of the retractor to move at least one ipsilateral iliac vessel posteriorly and laterally; and
using a second retraction blade of the retractor to move at least one contralateral iliac vessel anteriorly and laterally, wherein the ipsilateral iliac vessel and the contralateral iliac vessel are moved away from the anterolateral portion of the intervertebral space;
advancing the spinal implant at least partially into the intervertebral space between the L5 and S1 vertebrae via the anterolateral operative corridor, wherein the spinal implant is advanced into the intervertebral space at an oblique angle to the intervertebral space; and
rotating the spinal implant at least partially within the intervertebral space.

27. The method of claim 26, wherein the anterolateral operative corridor extends in an anterolateral direction to the anterolateral portion of the intervertebral space such that the anterolateral operative corridor provides access to the intervertebral space via the anterolateral direction.

28. The method of claim 27, wherein advancing the spinal implant to the intervertebral space comprises inserting the spinal implant at least partially into the intervertebral space in a first orientation such that the longitudinal axis of the implant is oriented substantially parallel to the anterolateral direction.

29. The method of claim 26, wherein the anterolateral operative corridor is oblique to the coronal plane of the subject and the median plane of the subject.

30. The method of claim 26, wherein the anterolateral operative corridor approximately bisects an angle formed between the coronal plane of the subject and the median plane of the subject.

31. The method of claim 26, wherein the anterolateral operative corridor comprises a pathway that extends substantially between a surface incision in the subject's skin and the intervertebral space.

32. The method of claim 26, wherein the retractor comprises a longitudinal axis, wherein the longitudinal axis of the retractor is positioned along an anterolateral path extending between an incision in the subject's skin and an implant insertion location proximate the anterolateral portion of the intervertebral space.

33. The method of claim 26, wherein rotating the spinal implant comprises rotating the spinal implant to an orientation such that the longitudinal axis of the implant is oriented substantially parallel to the coronal plane of the subject.

34. The method of claim 26, further comprising positioning a distal end of the first and the second retraction blades at an anterior face of a vertebra adjacent an anterior longitudinal ligament.

35. The method of claim 26, wherein the anterolateral operative corridor is at least partially obliquely positioned relative to an anterior face of the spinal disk between the L5 and S1 vertebrae.

36. The method of claim 26, wherein the spinal implant is advanced into the vertebral space between the L5-S1 vertebrae by advancing between the iliac vessels.

37. The method of claim 26, wherein the anterolateral operative corridor is substantially anterior to the psoas muscle.

38. The method of claim 26, wherein the first and second retraction blades are inserted such that iliac vessels are separated apart such that one iliac vessel at least partially moves in an anterior direction and one iliac vessel at least partially moves in a posterior direction.

39. The method of claim 26, wherein iliac vessels are separated apart to create a space for advancing the spinal implant between the iliac vessels by moving one iliac vessel at least partially in an anterior direction and one iliac vessel at least partially in a posterior direction.

40. The method of claim 26, wherein the spinal implant is advanced into the vertebral space between the L5-S1 vertebrae by advancing between the iliac vessels, wherein the iliac vessels have been separated apart, to create a space for advancing the spinal implant, by moving one iliac vessel at least partially in an anterior direction and one iliac vessel at least partially in a posterior direction.

* * * * *